(12) United States Patent
Egashira et al.

(10) Patent No.: US 7,345,158 B2
(45) Date of Patent: Mar. 18, 2008

(54) ACTIN RELATED CYTOSKELETAL PROTEIN "LACS"

(75) Inventors: Kensuke Egashira, Fukuoka (JP); Shujiro Inoue, Fukuoka (JP)

(73) Assignee: Anges MG, Inc., Osaka (JP)

( * ) Notice: Subject to any disclaimer, the term of this patent is extended or adjusted under 35 U.S.C. 154(b) by 19 days.

(21) Appl. No.: 10/526,109

(22) PCT Filed: Mar. 25, 2003

(86) PCT No.: PCT/JP03/03613

§ 371 (c)(1),
(2), (4) Date: Sep. 20, 2005

(87) PCT Pub. No.: WO2004/022753

PCT Pub. Date: Mar. 18, 2004

(65) Prior Publication Data

US 2006/0241068 A1    Oct. 26, 2006

(30) Foreign Application Priority Data

Aug. 30, 2002 (JP) .............................. 2002-255442

(51) Int. Cl.
*C07H 21/00* (2006.01)
*A61K 38/00* (2006.01)

(52) U.S. Cl. ..................................... 536/23.1; 530/356
(58) Field of Classification Search ................ 536/23.1; 530/356
See application file for complete search history.

(56) References Cited

U.S. PATENT DOCUMENTS

2002/0110804 A1   8/2002   Stanton

FOREIGN PATENT DOCUMENTS

WO    WO01/55326 A3 *  8/2001
WO    WO 01/74901 A2   10/2001

OTHER PUBLICATIONS

Brower et al. (1995) Genetic analysis of the fimbrin-actin binding interaction in *Saccharomyces cerevisiae*. Genetics. vol. 140, No. 1, pp. 91-101.*
Karlin et al. (1993) Applications and statistics for multiple high-scoring segments in molecular sequences. Proc Natl Acad Sci U S A. vol. 90, No. 12, pp. 5873-5877.*
Cros et al. (2001) Analysis of altered gene expression in rat soleus muscle atrophied by disuse. J. Cell. Biochem. vol. 83, No. 3, pp. 508-519.*
Lehrer-Graiwer, Joshua E., et al.; "Nitric oxide mediated induction of cytochrome c oxidase mRNA and protein in a mouse macrophage cell line;" *Neuroscience Letters*; Jul. 14, 2000; pp. 107-110; 288:2.
Kataoka, Chu, et al.; "Important role of Rho-kinase in the pathogenesis of cardiovascular inflammation and remodeling induced by long-term blockage of nitric oxide synthesis in rats;" *Hypertension*; 2002; pp. 245-250; 37:245.
Lehrer-Graiwer, Joshua E., et al.; "Nitric oxide mediated induction of cytochrome c oxidase mRNA and protein in a mouse macrophage cell line;" *Neuroscience Letters*; Jul. 14, 2000; pp. 107-110; 288:2.
Shujiro, Inoue, et al.; "Identification of a novel gene involved in the pathogenesis of cardiac hypertrophy in rats;" *Japanese Circulation Journal*; Mar. 31, 2002; p. 765; 66: (Supplement 1).
Takaori, Kazuo, et al.; "Inhibition of nitric oxide synthase causes cardiac phenotypic modulating In rat;" *European Journal of Pharmacology*; Mar. 12, 1997; pp. 59-62: 322:1.
Kataoka, Chu, et al.; "Important Role of Rho-kinase in the Pathogenesis of Cardiovascular Inflammation and Remodeling Induced by Long-Term Blockade of Nitric Oxide Synthesis in Rats;" *Hypertension*; Feb. 2002; pp. 245-250; 39:2.

* cited by examiner

*Primary Examiner*—Kathleen Kerr Bragdon
*Assistant Examiner*—Samuel Wei Liu
(74) *Attorney, Agent, or Firm*—Townsend and Townsend and Crew LLP

(57) ABSTRACT

The present invention provides the novel L-NAME-related actin cytoskeletal protein (LACS) and genes encoding the protein.

4 Claims, No Drawings

SEQUENCE LISTING

<160> NUMBER OF SEQ ID NOS: 2

<210> SEQ ID NO 1
<211> LENGTH: 3302
<212> TYPE: PRT
<213> ORGANISM: Rattus rattus

<400> SEQUENCE: 1

| | | | | | | | | | | | | | | |
|---|---|---|---|---|---|---|---|---|---|---|---|---|---|---|
| Met | Ala | Arg | Tyr | Gln | Ala | Ala | Val | Ser | Arg | Gly | Asp | Thr | Arg | Ser | Phe |
| 1 | | | | 5 | | | | | 10 | | | | | 15 | |
| Ser | Ala | Asn | Val | Met | Glu | Glu | Ser | Asp | Leu | Ser | Thr | Val | Pro | Gly | Gly |
| | | | 20 | | | | | 25 | | | | | 30 | | |
| Leu | Ala | Lys | Met | Lys | Arg | Gln | Phe | Glu | Lys | Asp | Glu | Met | Thr | Ser | Thr |
| | | | 35 | | | | | 40 | | | | | 45 | | |
| Cys | Asn | Ala | Phe | Ser | Glu | Tyr | Gln | Tyr | Gln | His | Glu | Ser | Arg | Ser | Glu |
| | | | 50 | | | | | 55 | | | | | 60 | | |
| Gln | Glu | Ala | Ile | His | Asn | Arg | Gln | Glu | Ile | Arg | Arg | Asn | Glu | Glu | Glu |
| 65 | | | | | 70 | | | | | 75 | | | | | 80 |
| Val | Ser | Lys | Gly | His | Arg | Thr | Asp | Val | Phe | Lys | Ala | Glu | Met | Met | Ser |
| | | | | 85 | | | | | 90 | | | | | 95 | |
| His | Leu | Glu | Lys | His | Thr | Glu | Glu | Thr | Asn | Gln | Ala | Ser | Gln | Phe | Arg |
| | | | 100 | | | | | 105 | | | | | 110 | | |
| Gln | Tyr | Val | Gln | Glu | Thr | Val | Ile | Asp | Thr | Pro | Glu | Asp | Glu | Glu | Ile |
| | | | 115 | | | | | 120 | | | | | 125 | | |
| Pro | Lys | Val | Ser | Thr | Lys | Ile | Leu | Lys | Glu | Gln | Phe | Glu | Lys | Thr | Ala |
| | 130 | | | | | 135 | | | | | 140 | | | | |
| Gln | Glu | Asn | Phe | Leu | Tyr | Ser | Asp | Lys | Glu | Thr | Thr | Pro | Ala | Lys |
| 145 | | | | | 150 | | | | | 155 | | | | | 160 |
| Cys | Ile | Lys | Ile | Glu | Asn | Asp | Ser | Glu | Glu | Thr | Leu | Lys | Pro | Ser | Ser |
| | | | | 165 | | | | | 170 | | | | | 175 | |
| Ala | Met | Gly | Thr | Ser | Ser | Tyr | Thr | Ser | Ala | Arg | Gln | Ser | Lys | Glu | Thr |
| | | | 180 | | | | | 185 | | | | | 190 | | |
| Ser | Thr | Ser | Ser | Tyr | Ser | Asn | His | Ser | Leu | Thr | Ser | Thr | Ile | Leu | Ala |
| | | | 195 | | | | | 200 | | | | | 205 | | |
| Gln | Glu | Lys | Gly | Thr | Pro | Ser | Gly | Lys | Met | Glu | Glu | Phe | Pro | Pro |
| | 210 | | | | | 215 | | | | | 220 | | | | |
| Pro | Pro | Asp | Val | Phe | Gln | Thr | Pro | Met | Asp | Val | Thr | Ala | Phe | Ser | Gln |
| 225 | | | | | 230 | | | | | 235 | | | | | 240 |
| Ser | Pro | Glu | Phe | Pro | Ser | Pro | Arg | Arg | Leu | Pro | Met | Pro | Arg | Asp |
| | | | | 245 | | | | | 250 | | | | | 255 | |
| Val | Tyr | Ser | Lys | Gln | Arg | Asn | Leu | Tyr | Glu | Leu | Asn | Arg | Leu | Tyr | Arg |
| | | | 260 | | | | | 265 | | | | | 270 | | |
| His | Ile | His | Pro | Glu | Leu | Arg | Lys | Asn | Leu | Glu | Lys | Asp | Tyr | Ile | Ser |
| | | | 275 | | | | | 280 | | | | | 285 | | |
| Glu | Val | Ser | Glu | Ile | Val | Ser | Ser | His | Ile | Asn | Ser | Gly | Asn | Ser | Ile |
| | 290 | | | | | 295 | | | | | 300 | | | | |
| Ser | Ala | Gly | Val | Gln | Gln | Ala | Arg | Tyr | Val | Phe | Glu | Asn | Thr | Asn | Asp |
| 305 | | | | | 310 | | | | | 315 | | | | | 320 |
| Ser | Ser | Gln | Lys | Asp | Leu | Ser | Ser | Glu | Arg | Glu | Asn | Leu | Glu | Trp | Asp |
| | | | | 325 | | | | | 330 | | | | | 335 | |
| Glu | Ile | Leu | Lys | Gly | Glu | Val | Gln | Ser | Ile | Arg | Trp | Ile | Phe | Glu | Asn |
| | | | 340 | | | | | 345 | | | | | 350 | | |
| Gln | Pro | Leu | Asp | Ser | Ile | Asn | Gln | Gly | Phe | Thr | Asp | Glu | Ala | Tyr | Thr |

-continued

```
            355                 360                 365
Ser Lys Gly Ile Ala Asp Gln Glu Leu Ile Ala Gly Asp Val Lys
    370                 375                 380

Tyr Thr Thr Trp Met Phe Glu Thr Gln Pro Ile Asp Ala Leu Gly Val
385                 390                 395                 400

Pro Ser Ala Gly Thr Glu Glu Asn Thr Glu Lys Ile Pro Glu Leu Ala
                405                 410                 415

Lys Gly Asp Val Cys Thr Ala Arg Trp Met Phe Glu Thr Arg Pro Leu
                420                 425                 430

Asp Ser Met Asn Lys Met His Glu Trp Glu Asp Glu Thr Ala Ser Thr
            435                 440                 445

Phe Ile Lys Asp Ile Thr Gly Gly Asp Val Lys Thr Val Arg Tyr Met
450                 455                 460

Phe Glu Thr Gln Gln Leu Asp Gln Leu Gly Gln Leu His Ser Val Asp
465                 470                 475                 480

Glu Met Asn Leu Leu Gln Leu Arg Ser Glu Leu Lys Glu Ile Lys Gly
                485                 490                 495

Asn Val Lys Arg Ser Ile Lys Cys Phe Glu Thr Gln Pro Leu Tyr Val
                500                 505                 510

Ile Arg Asp Gly Ser Gly Gln Met Leu Glu Ile Lys Thr Val Gln Arg
                515                 520                 525

Glu Asp Ile Glu Lys Gly Asp Val Arg Thr Ala Arg Trp Met Phe Glu
            530                 535                 540

Thr Gln Pro Leu Asp Thr Ile Lys Gln Asp Ile Thr Glu Ile Lys Val
545                 550                 555                 560

Val Arg Gly Ile Ser Met Glu Glu Asn Val Lys Gly Glu Val Gly Arg
                565                 570                 575

Ala Arg Trp Leu Phe Glu Thr Gln Pro Leu Glu Lys Ile Lys Glu Glu
                580                 585                 590

Ser Gly Glu Ala Val Leu Lys Thr Glu Ala Val Val Gly Ile Asp Val
            595                 600                 605

Ser Lys Lys Cys Trp Met Phe Glu Thr Gln Pro Leu Asp Thr Leu Lys
            610                 615                 620

Gln Ser Pro Asp Thr Glu Ser Val Ser Pro Glu Glu Arg Ile Gly Gly
625                 630                 635                 640

Asp Val Lys Thr Thr Lys His Leu Leu Glu Thr Leu Pro Ile Glu Ala
                645                 650                 655

Leu Lys Asp Ser Pro Asp Val Gly Lys Leu Gln Lys Ile Thr Ala Ser
                660                 665                 670

Glu Glu Glu Lys Gly Asp Val Lys His Gln Lys Trp Val Phe Glu Thr
            675                 680                 685

Gln Arg Leu Glu Asp Ile Arg Glu Asp Lys Lys Glu Tyr Thr Gln Thr
            690                 695                 700

Val Lys Leu Glu Ala Val Asp Arg Gly His Val Lys Asn Glu Thr His
705                 710                 715                 720

Ile Phe Glu Ser Asn Asn Leu Ile Lys Val Asp Ala Ser His Gln Ile
                725                 730                 735

Glu Val Glu Gly Val Thr Arg Gly Thr Val Glu Leu Asn Lys Ser Leu
                740                 745                 750

Phe Glu Thr Thr Pro Leu Tyr Ala Ile Gln Asp His Leu Gly Lys Tyr
            755                 760                 765

His Gln Val Lys Thr Val Gln Gln Glu Glu Ile Val Arg Gly Asp Val
            770                 775                 780
```

-continued

```
Arg Ser Cys Arg Trp Leu Phe Glu Thr Arg Pro Ile Asp Gln Phe Asp
785                 790                 795                 800

Glu Ser Leu His Lys Phe Gln Ile Ile Arg Gly Ile Ser Ala Gln Glu
                805                 810                 815

Ile Gln Ala Gly Asn Val Lys Ser Ala Arg Trp Leu Phe Glu Thr Gln
            820                 825                 830

Pro Leu Asp Ser Ile Lys Tyr Phe Ser Asn Val Glu Glu Thr Asp Ser
        835                 840                 845

Lys Thr Glu Gln Ser Thr Asp Ile Val Lys Gly Asp Val Lys Thr Cys
850                 855                 860

Lys Trp Leu Phe Glu Thr Gln Pro Met Glu Ser Leu Tyr Glu Lys Ala
865                 870                 875                 880

Ser Leu Met Thr Asn Ser Glu Asp Ile His Lys Gly Asp Val Arg Thr
                885                 890                 895

Cys Met Trp Leu Phe Glu Thr Gln Pro Leu Asp Ala Ile Lys Asn Asp
            900                 905                 910

Ser Glu Ala Thr Val Lys Leu Gln Thr Val Lys Gln Glu Ile Gln
        915                 920                 925

Gly Gly Asp Val Arg Thr Ala Cys Leu Leu Phe Glu Thr Glu Asn Leu
930                 935                 940

Asp Asn Ile Gln Gly Gly Glu Gly Lys Glu Thr Lys Pro Val Glu Met
945                 950                 955                 960

Asp Ile Glu Ser Gly Asp Val Ser Gly Met Lys Tyr Lys Phe Glu Asn
                965                 970                 975

Gln Ser Leu Asp Ser Ile Ser Cys Ser Ser Glu Asn Val Leu Asn Lys
            980                 985                 990

Ile Lys Thr Leu Lys Ile Glu Asp Ile Gln Lys Gly Asn Val Leu Asn
        995                 1000                1005

Cys Arg Trp Leu Phe Glu Asn Gln Pro Ile Asp Met Ile Lys Glu Asn
    1010                1015                1020

Gln Glu Gly Asp Gly Leu Val Lys Thr Val Thr Asp Ile Gln Gly Gly
1025                1030                1035                1040

Asp Val Arg Lys Gly Cys Phe Ile Phe Glu Thr Phe Ser Leu Asp Glu
                1045                1050                1055

Ile Lys Asp Glu Ser Asp Val Ile Ser Thr Arg Gln Thr Asn Thr Glu
            1060                1065                1070

Glu Val Ile Lys Gly Asp Val Lys Ser Tyr Lys Met Leu Phe Glu Thr
        1075                1080                1085

Gln Pro Leu Tyr Ala Ile Gln Asp Gln Glu Gly Phe Tyr His Glu Val
    1090                1095                1100

Thr Thr Val Lys Lys Glu Glu Thr Ile His Gly Asp Val Arg Gly Thr
1105                1110                1115                1120

Arg Trp Leu Phe Glu Thr Lys Pro Leu Asp Ser Ile Asn Ala Ser Glu
                1125                1130                1135

Asp Val Tyr Ile Ile Lys Ser Val Thr Gln Glu Asp Ile Gln Lys Gly
            1140                1145                1150

Asp Val Ser Ser Val Arg Tyr Arg Phe Glu Thr Gln Pro Leu Asp Met
        1155                1160                1165

Ile Ser Asp Lys Ser His Asn Ile Met Pro Thr Ile Asp His Ile Gln
    1170                1175                1180

Gly Gly Asn Val Gln Met Asn Lys Gln Leu Phe Glu Ser Glu Gly Gly
1185                1190                1195                1200
```

-continued

```
Asp Lys Lys Asn Tyr Val Arg Thr Val Ser Ile Asn Glu Ile Gln Lys
            1205                1210                1215
Gly Asn Val Lys Thr Ser Thr Trp Leu Phe Glu Thr His Ser Ile Asp
        1220                1225                1230
Glu Leu Gly Glu Val Ser Thr Tyr Glu Asn Ile Lys Thr Val Thr Gln
    1235                1240                1245
Glu Asp Val Gln Lys Gly Asp Val Lys Gln Ala Val Trp Leu Phe Glu
1250                1255                1260
Asn Gln Thr Leu Asp Ser Ile Lys Glu Leu Asp Glu Ser Asp Thr Lys
1265                1270                1275                1280
Ile Thr Lys Glu Glu Ile Pro Pro Ser Asp Val Lys Thr Thr Thr Trp
            1285                1290                1295
Leu Phe Glu Thr Thr Pro Ile His Glu Phe Asn Glu Thr Arg Ile Glu
        1300                1305                1310
Lys Glu Glu Ile Ile Gly Lys Ser Ile Lys Glu Thr Leu Glu Asp Leu
    1315                1320                1325
Tyr Ser Gln Arg Val Val Glu Ala Pro Gly Ile Ile Glu Ala Asp
1330                1335                1340
Glu Val Gly Asp Val Arg Met Ala Lys Tyr Lys Leu Met Asn Gln Arg
1345                1350                1355                1360
Thr Pro Glu Ile Gln Lys Glu Val Ile Arg Ala Asp Leu Gly Asn
            1365                1370                1375
Ile Met Met Asn Leu Leu Ser Gln Arg Asp Cys Thr Lys Lys Glu Ile
        1380                1385                1390
Phe Ile Ser Glu Glu Lys Gly Asn Val Asn Phe Thr Lys Thr Gln
    1395                1400                1405
Leu Leu Asn Arg Ser Met Glu Phe His Ala Glu Lys Glu Glu Ile Val
    1410                1415                1420
Arg Gly Asp Val Lys Gln Ala Ile Gln Lys Leu Phe Ser Glu Glu Arg
1425                1430                1435                1440
Cys Ala Lys Arg Gly Ile Leu Ile Gln Glu Asp Glu Lys Gly Asp Val
            1445                1450                1455
Asn Met Thr Ile Tyr Cys Leu Leu His Glu Asn Ala Gly Asp Lys Thr
        1460                1465                1470
Lys Arg Glu Asp Ile Leu Gly Gly Asp Val Arg Arg Thr Ile His Asn
    1475                1480                1485
Leu Leu Ser Ser Ala Ser Asn Asp Lys Ile Ser Glu Arg Thr Lys Ile
    1490                1495                1500
Asp Ala Ser Glu Arg Gly Asn Val Gln Phe Phe Thr Thr Cys Ile Glu
1505                1510                1515                1520
Thr Gly Ala Leu Asp Tyr Leu Lys Gln Leu Gln Thr Gly Ser Asn Glu
            1525                1530                1535
Thr Leu Thr Ala Arg Lys Gln Glu Gly Glu Glu Ile Ile Gly Gly
        1540                1545                1550
Asp Val Glu Gly Thr Lys Phe Leu Leu Lys Lys Arg Gln Ser Ser Ile
    1555                1560                1565
Glu Arg Thr Val Ser Glu Thr Asp Ile Ile Pro Gly Asp Val Arg Asn
    1570                1575                1580
Thr Val Lys Val Phe Met Thr Glu Pro Gln Ser Ala Ser Phe Lys Thr
1585                1590                1595                1600
Ala Lys Glu Glu Ile Val Lys Gly Asp Leu Lys Ser Thr Leu Asn Ser
            1605                1610                1615
Leu Asn Gln Ala Met Asn Gln Lys Val Val Ala Lys Thr Glu Asp Ile
```

-continued

```
                 1620                1625                1630
Met Lys Asp Asp Lys Ala Ala Ile Leu Lys Ser Leu Lys Glu Ser Gly
       1635                1640                1645

Gly Arg Gln Lys Glu His Lys Gln Ser Ala Ser Ile Ser Ser Asp Ile
   1650                1655                1660

Gly Gln Ala Ile Glu Cys Leu Glu Lys Ala Thr Asn Thr Arg Thr Glu
1665                1670                1675                1680

Ile Leu Lys Lys Glu Leu Ile Leu Asp Asp Leu Lys Thr Ser Leu Arg
       1685                1690                1695

Ser Leu Lys Glu Glu Gln Tyr Ser Phe Lys Glu Val Gly Lys Gln Gly
       1700                1705                1710

Met Val Lys Asp Val Leu Gly Phe Ser Glu Arg Gln Glu Leu Gly Ile
       1715                1720                1725

His Pro Ala Ala Val Gln Arg Glu Lys Lys Ser Leu Leu Gln Pro Val
       1730                1735                1740

Pro Gly Pro Cys Glu Pro Ala Ile Arg Gln Gln Ala Gly Pro Gly Pro
1745                1750                1755                1760

Leu Asp Glu Ala Thr Gln Lys Ser Cys His Arg Ser Leu Thr Glu Glu
       1765                1770                1775

Arg Thr Glu Ala Asn Leu Pro Lys Ala Pro Lys Gly Thr Val Lys Ile
       1780                1785                1790

Val Ile Asp Arg Glu Gln Asn Asn Asp Ala Leu Glu Lys Ser Leu Arg
       1795                1800                1805

Lys Met Ser Asn Ser Glu His Arg Ala Met Lys Asn Val Leu Asp Met
       1810                1815                1820

Gly Asp Arg Arg Gly Val Trp Thr Glu Ser Lys Glu Cys Leu Cys Ser
1825                1830                1835                1840

Asp Asp His Met Ser Lys Tyr Val Ser Ala Ser Met Ser Arg Lys Lys
       1845                1850                1855

Ser Leu Lys Thr Lys Glu Ser Glu Asn Val Arg Glu Ser Lys Asp Asp
       1860                1865                1870

Val Ser Ser Thr Gln Ser Val Asp Lys Thr Phe Arg Lys Gln Gln Thr
       1875                1880                1885

Gln Asn Cys Glu Leu Gly Lys Asp His Gln Lys Ser Gln Phe Gln Asp
       1890                1895                1900

Ser Tyr Ala Lys Asn Gln Lys Asn Thr Gln Asn Ile Ser Met Ser Ala
1905                1910                1915                1920

Glu Thr Gln Ser Tyr Arg Pro Asp Pro Thr Gln His Pro Val Ser Asn
       1925                1930                1935

Pro Ala Gly Glu Thr Leu Glu Met Thr Arg Asp Phe Gln Lys Gln Ala
       1940                1945                1950

Leu Ile Arg Gln Glu Lys Gln Asn Ser Asn Lys Asp Met Arg Lys Asn
       1955                1960                1965

Asp Met Gly Leu Gln Pro Leu Pro Val Gly Lys Asp Ala His Ser Ala
       1970                1975                1980

Pro Gly Val Thr Val Ser Gly Lys Asn His Lys Arg Thr Gln Ala Pro
1985                1990                1995                2000

Asp Lys Lys Gln Arg Ile Asp Val Cys Leu Glu Ser Gln Asp Phe Leu
       2005                2010                2015

Met Lys Thr Asn Thr Ser Lys Glu Leu Lys Met Ala Met Glu Arg Ser
       2020                2025                2030

Phe Asn Pro Val Asn Leu Tyr Pro Asp Cys Gly Val Lys Glu Asn Glu
       2035                2040                2045
```

```
Asp Ala Leu Pro Pro Pro Ser Pro Pro Pro Pro Pro Ser Asn Ala
    2050                2055                2060

Ser Ser Glu Ile Glu Phe Pro Leu Pro Pro Pro Pro Ile Met Leu
2065                2070                2075                2080

Leu Pro Glu Lys Asn Glu Phe Pro Pro Ser Ser Pro Thr Glu Lys Ser
        2085                2090                2095

Arg Ala Glu Leu Glu Ser Leu Pro Thr Leu Pro Leu Pro Pro Pro
        2100                2105                2110

Gly Asp Glu Lys Ser Asp Gln Glu Cys Leu Pro Thr Ser Leu Pro Pro
        2115                2120                2125

Pro Pro Pro Thr Ala Pro Ser Gln Pro Ala His Leu Leu Ser Ser Ser
    2130                2135                2140

Val Leu Glu His His Ser Glu Ala Phe Leu Gln Gln Tyr Ser Arg Lys
2145                2150                2155                2160

Glu Thr Leu Asp Ser His Gln Leu His Ser Gln Ala Lys Ile Leu Thr
            2165                2170                2175

Gly Lys Ser Pro Pro Pro Thr Leu Pro Lys Pro Lys Leu Pro Glu Arg
        2180                2185                2190

Ile Lys Ala Lys Met Ser Gln Asp Ser Pro Ser Gly Glu Leu Glu Arg
        2195                2200                2205

Ser Leu Ser Asp Val Glu Ile Lys Thr Thr Leu Ser Lys Asp Gln Lys
    2210                2215                2220

Ser Ser Leu Val Ala Glu Ser Arg Glu His Thr Glu Ala Lys Gln Glu
2225                2230                2235                2240

Val Phe Arg Lys Ser Leu Gly Arg Lys Gln Leu Ser Ile Ser Ser Ala
            2245                2250                2255

Asn Ser Leu Ser Gln Thr Val Pro Glu Ile Pro Ala Pro Lys Glu Lys
            2260                2265                2270

Gln Thr Ala Pro Leu Val Lys Ser His Ser Phe Pro Ser Gly Ser Glu
        2275                2280                2285

Gln Gln Ser Pro Lys Pro Tyr Met Arg Lys Phe Lys Thr Pro Leu Met
    2290                2295                2300

Ile Ala Glu Glu Lys Tyr Arg Gln Gln Arg Glu Glu Leu Glu Lys Gln
2305                2310                2315                2320

Arg Arg Glu Ser Ser Cys His Ser Ile Ile Lys Thr Glu Thr Gln His
            2325                2330                2335

Arg Ser Leu Ser Glu Lys Glu Lys Glu Thr Glu Leu Gln Lys Ala Ala
        2340                2345                2350

Glu Ala Met Ser Thr Pro Arg Lys Asp Ser Asp Phe Thr Arg Ala Gln
        2355                2360                2365

Pro Asn Leu Glu Pro Lys Ser Lys Ala Val Ile Ala Ser Glu Cys Ser
    2370                2375                2380

Glu Ser Gln Leu Ser Thr Ala Ser Ala Leu Thr Val Ala Thr Glu Arg
2385                2390                2395                2400

Leu Gln His Val Leu Ala Ala Ser Asp Asp Lys Leu Thr Leu Arg Arg
            2405                2410                2415

Glu Gly Thr Gln Asn Ser Ser Asp Thr Leu Gln Ser Lys Thr Ala Cys
        2420                2425                2430

Glu Ile Asn Gln Ser His Lys Glu Cys Arg Thr Glu Gln Thr Phe Glu
        2435                2440                2445

Gln His Val Glu Lys Leu Pro Phe Pro Gln Thr Lys Pro Ile Ser Pro
    2450                2455                2460
```

```
Ser Phe Lys Val Lys Thr Ile Arg Leu Pro Ala Leu Asp His Thr Leu
2465                2470                2475                2480

Thr Glu Thr Asp Leu Ser Ser Glu Arg Arg Val Lys Gln Ser Glu Ile
            2485                2490                2495

Asp Val Gln Thr Ser Thr Lys Glu Met Asn Lys Glu Ile Lys Lys Thr
        2500                2505                2510

Glu Val Ser Thr Gln Cys Asp Asn Lys Gln Ser Val Ala Glu Lys Tyr
    2515                2520                2525

Phe Gln Leu Pro Lys Thr Glu Lys Arg Val Thr Val Gln Met Pro Lys
2530                2535                2540

Asp Tyr Ala Ala Lys Ser His Gln Ser Lys Leu Gln Thr Val Pro Lys
2545                2550                2555                2560

Lys His Gly Gly Leu Gly Glu Phe Asp Arg Gly Asn Val Leu Gly Arg
            2565                2570                2575

Glu Gly Lys Asn Gln Asp Ser Ser Met Ser Ser Thr Lys Glu Ser Arg
        2580                2585                2590

Val Ile Val Glu Arg Lys Gln Glu His Leu Gln Asp Gln Ser Val Pro
    2595                2600                2605

Arg Leu Val Gln Gln Lys Ile Ile Gly Glu Ser Leu Asp Ser Arg Val
2610                2615                2620

Gln Asn Phe Gln Gln Thr Gln Thr Gln Thr Ser Arg Ile Glu His Lys
2625                2630                2635                2640

Glu Leu Ser Gln Pro Tyr Ser Glu Lys Lys Cys Leu Arg Asp Lys Asp
            2645                2650                2655

Lys Gln Gln Lys Gln Val Ser Ser Asn Thr Asp Asp Ser Lys Gln Glu
        2660                2665                2670

Ile Thr Gln Lys Gln Ser Ser Phe Ser Ser Val Arg Glu Ser Gln Gln
    2675                2680                2685

Asp Gly Glu Lys Cys Ala Ile Asn Ile Leu Glu Phe Leu Arg Lys Arg
2690                2695                2700

Glu Glu Leu Gln Gln Ile Leu Ser Arg Val Lys Gln Phe Glu Ala Asp
2705                2710                2715                2720

Ser Asn Lys Ser Gly Leu Lys Thr Phe Gln Thr Leu Leu Asn Ile Ala
            2725                2730                2735

Pro Val Trp Leu Ile Ser Glu Glu Lys Arg Glu Tyr Gly Val Arg Val
        2740                2745                2750

Ala Met Glu Asn Asn Leu Glu Lys Val Lys Glu Glu Ile His Ile
    2755                2760                2765

Lys Thr Gln Ala Glu Glu Met Leu Val His Cys Glu His Val Ile Arg
    2770                2775                2780

Thr Ala Met Met Ala Ser Gln Thr Gly Lys Gln Lys Asp Lys Pro Thr
2785                2790                2795                2800

Asn Leu Asn Glu Met Pro Leu Lys Val Ser Asn Val Asn Leu Ser Ser
            2805                2810                2815

His Lys Gly Thr Glu Gln Lys Glu Ser Lys Ile Val Glu Glu Lys Leu
        2820                2825                2830

Ala Ser Arg Gln Val Ala Thr His Ser Glu Ala Ala Thr His Asn Pro
    2835                2840                2845

Ala Lys Thr Tyr Gln Glu Ala Lys Gly Asp Asp Ser Lys Met Ala Pro
    2850                2855                2860

Pro Ser Leu Lys Thr Arg Pro Pro Ser Pro Thr Phe Ile Thr Ile Glu
2865                2870                2875                2880

Ser Thr Ala Arg Arg Ala Glu Thr Ser Thr Lys Ser Glu Leu Ser Gln
```

-continued

```
                  2885                2890                2895
Ser Pro Lys Asn Asn Ser Cys Val Glu Pro Leu Pro Arg Arg Pro Met
            2900                2905                2910
Glu His Thr Ser Arg Leu Pro Arg Thr Ser Thr Ser Pro Ser Pro Pro
            2915                2920                2925
Arg Ser Arg Ser Glu Gln Leu Val Arg Leu Lys Asp Thr Thr Ala Arg
            2930                2935                2940
Leu Ala Lys Gly Thr Ile Pro Cys Ser Pro Gly Thr Pro Val Pro Val
2945                2950                2955                2960
Val Glu Lys Arg Ser Glu Val Val Met Ser Pro Ala Thr Leu Arg Arg
            2965                2970                2975
Gln Ile Lys Ile Glu Ser Arg Gly Gly Asp Ser Pro Thr Ile Thr
            2980                2985                2990
Ile Pro Val Ser Val Asn His His Val Val Ser Gly Ser Phe Arg Glu
            2995                3000                3005
Ser Val Asp Ala Gln Glu Ala Val Lys Lys Thr Glu Lys Thr Glu Thr
            3010                3015                3020
Tyr Val His Lys Asp Lys Lys Asn Ser Val Ser Ser Ala Met Pro Glu
3025                3030                3035                3040
Thr Glu Ser Tyr Asp Ala Val Glu Ile Ile Arg Lys Val Glu Gly Pro
            3045                3050                3055
His Leu Ser Glu His Arg Glu Arg Phe Glu Ala Thr Asn Gln Thr Val
            3060                3065                3070
Gln Met Ala Glu His Phe Leu Asn Gly His Glu Asn Glu Val Asn Arg
            3075                3080                3085
Trp Phe Arg Glu Phe Glu Asn Gly Pro Val Phe Gly Ala Lys Thr Glu
            3090                3095                3100
Arg Arg Ala Tyr Ala Asn Gly Glu Ile Asn His Asn Met Lys Gln Glu
3105                3110                3115                3120
Ser His Thr Phe Cys Lys Glu Glu Phe Gly Leu Glu Ser Ser Glu Thr
            3125                3130                3135
Ala Asn Phe Thr Gly Phe Ser Tyr Arg His Pro Arg Glu His Arg Ala
            3140                3145                3150
Lys Ala Pro Ala Thr Gln Pro Arg Val His Ser Glu Ala Arg Ala Leu
            3155                3160                3165
Asn Glu His Phe Leu Ser Val Asp Ala Phe Asp Ser Gln Ile Val Glu
            3170                3175                3180
Ser Gln Val Ala Thr Ser Ser Arg Ser Ser Glu Ala Gly Arg Ser
3185                3190                3195                3200
Gly Phe Asp Phe Lys His Ala Pro Pro Thr Tyr Glu Asp Val Ile Ala
            3205                3210                3215
Gly His Ile Leu Asp Ile Ala Asp Ser Pro Thr Asn Leu Arg Arg Asn
            3220                3225                3230
Phe Gln Lys Thr Trp Gln Glu Ser Glu Arg Val Phe Lys Ser Val Gly
            3235                3240                3245
Tyr Glu Thr Ser Asp Ala His Ala Thr Glu Met Ser Arg Ala Phe Gln
            3250                3255                3260
Glu Glu Leu Ala Phe Leu Ser Glu Thr Val Gly Pro Arg Gln Gly Asn
3265                3270                3275                3280
Leu His Asn Leu Ser Lys Asp Gly Leu Ser Asn Gly Val Pro Arg Ser
            3285                3290                3295
Arg Pro Ala Glu Phe Ser
            3300
```

<210> SEQ ID NO 2
<211> LENGTH: 12178
<212> TYPE: DNA
<213> ORGANISM: Rattus rattus

<400> SEQUENCE: 2

```
agctggtctc cactctgctg gttgctttca ggggactggg aaatttgctg tatctcaaac      60
agggaggaac cttccgagtg aagagttgca aatccataga gcatttctac ggagataggg     120
tcaattctgg tacaaagaga ccttcaacct tactaagccg ggagacgtga gtactgctgg     180
gactgaggac cagtcggatc tcctagaggc gctgtccctg aaggagagga tggctaggta     240
ccaggcagct gtttcacggg gcgacacccg cagcttctcg gctaatgtca tggaagaatc     300
agacttgtgc accgtgcctg gtggtttagc caagatgaag agacaatttg aaaaggatga     360
aatgacttca acctgcaatg ccttctctga gtatcaatac caacatgaga gcagatctga     420
gcaggaggca atccacaaca ggcaagaaat aagaaggaat gaagaagaag tttctaaagg     480
acacagaact gatgtcttca agctgaaat gatgtcacat cttgaaaagc acacggagga     540
aacaaaccaa gcttcacagt tcgtcaata tgttcaagaa acagtcattg atacaccaga     600
agacgaagag attcctaagg tttccactaa gattttaaaa gagcaatttg aaaagactgc     660
ccaggaaaac ttcctctact ctgataaaga acaacaacc ccagccaagt gtataaagat     720
tgaaaatgac agtgaagaaa ccttaaagcc atcatcggct atgggtacct cttcttatac     780
ttcagccagg caaagcaagg aaacttcaac ctcaagttat agtaatcaca gtctgacttc     840
aacaatcctg gcacaagaaa agggcactcc ttcaggaaag atggaagaat ttcctcctcc     900
cccacctgat gtttttcaaa caccaatgga tgtgacagca ttttcccagt ccctgaatt     960
ccccagccct cctagaagac tgccaatgcc cagagatgta tattccaagc aacgaaattt    1020
gtatgaatta aaccgtttat ataggcatat ccatcctgag ttaagaaaaa acttagaaaa    1080
agattatatc agtgaggttt ctgaaattgt ttctagtcac ataaactcag ggaactcgat    1140
atcagcaggt gtacaacaag ctcggtatgt tttcgaaaat acgaatgaca gttctcagaa    1200
agatttgagc tcagaaagag aaaacctgga gtgggatgaa attctgaaag gagaggtgca    1260
gtcaattcga tggattttg agaatcagcc attagattct atcaaccaag gttttacaga    1320
tgaagcgtac acttccaaag gcattgctga ccaagaactc attgctgggg gtgacgtgaa    1380
atatacgact tggatgtttg aaactcagcc aatagatgca ttgggagttc cttctgctgg    1440
cactgaagaa aacactgaga aaattcctga gctagctaaa ggagatgttt gcacagcaag    1500
gtggatgttt gaaacaaggc ctttagactc aatgaacaaa atgcatgaat gggaagatga    1560
aacggcatct acttttataa aggacataac tgggggagat gtcaagactg tgagatacat    1620
gtttgaaact caacaactgg atcaacttgg acagcttcac tcagtggatg aaatgaactt    1680
attacaactc agatcagagc tcaaagaaat taaggaaat gttaagagaa gcataaaatg    1740
tttcgaaact caaccactgt atgtcattag agatggttca ggccaaatgc tagaaattaa    1800
aactgtgcag agagaagaca ttgaaaaggg agatgtaagg acagcacgct ggatgtttga    1860
aacgcagcct ttggacacaa taaaacaaga catcacggaa attaaagttg ttcgaggaat    1920
atccatggag gaaaatgtca aggcgaggt gggtagagca aggtggttat ttgaaactca    1980
accactggag aaaatcaaag aagagtcagg tgaggctgtc ctgaaaacag aagcagttgt    2040
agggatagat gtgtctaaaa agtgttggat gtttgaaacg cagccattag acactctaaa    2100
```

-continued

```
acaatctcct gatacagaga gtgtatcacc tgaagagagg ataggaggtg acgtaaaaac    2160
caccaaacat ctgttagaaa cactcccaat agaggcctta aaagacagcc cagatgttgg    2220
aaagcttcaa aaaatcactg cctctgagga agaaaagggc gatgttaagc accaaaaatg    2280 ggttttttgaa actcaacgtt tagaagatat tagagaagat aagaaggaat atacccagac    2340
agtgaagcta aagcagtgg acagagggca tgtgaagaac tatacacata tcttcgaatc    2400
caataatcta attaaggttg atgcatcaca tcaaattgag gtggaaggag tcacaagagg    2460
cactgtggag ttgaataaat ctctctttga gacaacccca ctgtatgcca ttcaagacca    2520
tcttggaaaa taccaccaag taaagacagt ccagcaagaa gaaatagtaa ggggtgatgt    2580
aagaagctgt agatggcttt ttgaaacaag gcccattgac caatttgacg aaagccttca    2640
taaatttcag ataattagag gaatatctgc tcaagaaata caggcaggga atgtgaaatc    2700
agctaggtgg ctgtttgaga cccaacctct tgattcaatt aaatatttta gcaacgtgga    2760
agaaacagac agcaaaactg aacagagtac tgatattgtt aaggggatg tcaaaacctg    2820 taaatggcta tttgaaaccc agccaatgga gtctctttat gaaaaagctt ccttgatgac    2880
gaactcagaa gatattcaca aaggtgatgt tagaacttgt atgtggctat ttgaaactca    2940
gccacttgat gccataaaaa atgactctga agccacagta aaactgcaaa ctgtgaaaca    3000
ggaggagata caaggtgggg atgtccggac agcatgtctt cttttgaga cagaaaatct    3060 ggacaacata cagggcggtg aagggaaaga aacgaagccc gtggagatgg atatagaatc    3120
tggggatgtc tctggcatga agtataagtt tgaaaatcag tccttagact ctataagttg    3180
cagttcggag aatgtttga ataagatcaa aaccctaaaa atcgaagaca ttcagaaagg    3240
caatgtttta aattgtaggt ggctatttga aaatcaacct atcgatatga taaaagaaaa    3300
tcaagaaggt gatggattgg ttaagacagt gacagacata caggtggag atgtgagaaa    3360 gggatgcttc attttgaga cgttttcttt agatgagatt aaagatgcct ctgatgtcat    3420
cagcaccaga caaacaaata ccgaggaagt aataaaaggt gatgtaaaaa gctacaagat    3480 gcttttgaa acacaaccac tctatgcgat tcaagaccaa gaagggtttt atcatgaagt    3540
gacaacagtt aaaaaagaag aaactattca tggagatgta cgaggaacaa ggtggctctt    3600
tgaaacaaaa ccgttagact caattaacgc atcagaagat gtatacatta ttaaatctgt    3660
cactcaggaa gacattcaga agggggatgt gagttctgtc agataccgat ttgaaacaca    3720
accactggat atgatttcag acaaatcaca taatattatg cccactattg accatattca    3780
aggaggcaat gtgcagatga ataaacaact attcgagtct gaaggtggtg acaagaagaa    3840
ttatgtaaga acagtgagca tcaatgaaat acaaaagggc aatgttaaga cttctacttg    3900 gctcttttgaa actcacagca tagatgagct gggagaagtg tccacctatg aaaatatcaa    3960
gacagtcacc caggaagacg tgcagaaagg tgacgtgaag aaaatatcaa ggcttttttga    4020 aaatcagaca ttggattcca ttaaggaact tgatgaaagt gacaccaaaa taaccaaaga    4080
agaaattcct ccgtcagatg tcaagacaac aacgtggctc tttgaaacga cacctattca    4140
cgaatttaat gaaactagaa tagaaaagga agaaattatt ggtaaaagca ttaaagaaac    4200
cttggaagac ctctactctc aaagagtggt tgaagctccc ggaatcatca ttgaagctga    4260
tgaagttggg gatgtcagaa tggccaaata caagctcatg aaccaaagga ctcctgagat    4320
ccagaaggaa gaagttatca gagctgacct tggaaacata atgatgaact tgctttccca    4380
aagagactgc acaaaaaagg agatatttat cagtgaagag gagaagggaa atgtcaattt    4440 tactaaaaacc cagttattaa acagatcaat ggaattccat gctgaaaagg aagagatagt    4500
```

```
aagaggggat gtaaaacaag caatccaaaa gctgttctct gaggaaaggt gtgcaaagag    4560
aggcatatta attcaagaag atgaaaaggg agatgttaac atgactatct attgtcttct    4620
tcatgagaat gctggcgaca agactaagcg tgaagacata ctgggaggtg atgtgagaat    4680
cactattcat aacctgttgt cttccgcatc aaatgataaa atatctgaaa ggacaaaaat    4740
cgatgcatcg gagagggaa atgttcagtt cttcacaaca tgcatagaaa ctggagcttt    4800
ggattacctc aagcaactcc aaacagggtc aaatgaaaca ctcacagcta gaaagcaaga    4860
aggggaggaa gaaataattg gtggtgatgt tgagggaaca aaattcttac taaagaaaag    4920
acagtcttct attgaacgca ctgttagtga aactgatatc atcccaggag atgtgcgtaa    4980
tacagttaaa gtcttcatga cggagcccca gagtgcatct tttaagacag cgaaagaaga    5040
gattgtaaaa ggtgatttga aatcaaccct gaattctctc aaccaggcca tgaatcagaa    5100
agtagtggct aaaacagaag atattatgaa agatgacaag gcagctatac tcaagtcact    5160
taaggagtca ggtggcagac agaaagaaca taaacaatct gctagcatct ctagtgatat    5220
tgggcaagct attgagtgcc ttgaaaaggc cacaaataca aggacagaaa tattgaaaaa    5280
ggagctgata ttagatgatc ttaaaacatc attaaggtct ttgaaagaag aacaatacag    5340
tttcaaagag gttggtaaac agggaatggt caaagatgta ctaggattct cagagagaca    5400
agaactaggg attcatccag cagctgtcca gagagagaaa aaaagccttc ttcaaccagt    5460
gccaggacca tgtgagccag caatcaggca gcaagcagga ccaggccctc ttgatgaagc    5520
tacacagaaa tcctgccatc ggtctttaac agaagaaaga actgaggcta atcttcccaa    5580
agcccctaag ggcactgtaa agattgtcat tgatcgagaa caaaacaacg atgctcttga    5640 gaaaagccctt aggaaaatgt ctaattcaga acatagagct atgaaaaatg ttttagacat    5700
gggtgacaga aggggtgtct ggacagagag caaagagtgt ctgtgtagtg acgaccatat    5760
gagcaaatac gtaagtgcaa gcatgtcaag gaagaaaagt ctaaagacca aggaatcaga    5820
gaatgtgaga gaatcgaagg acgatgtgag ctccacccag tctgtggata aacatttag    5880 gaagcaacag actcaaaact gtgaactggg aaggatcac cagaagtctc agttccagga    5940
ttcctatgcg aagaatcaga aaaatacca aaacattagt atgtcagcag aaacccaaag    6000
ttacagacca gaccctaccc aacatccagt cagcaatcca gctggagaaa cgcttgagat    6060
gacaagggac tttcagaagc aagccttgat aagacaggaa aagcagaatt ctaataaaga    6120
tatgaggaaa aatgacatgg gccttcaacc tctgcctgta gggaaggacg cacacagtgc    6180
accaggagtg acagtctctg ggaaaaacca caaagaact caggcacctg acaagaaaca    6240
gagaattgat gtttgtctag aaagccagga cttttctaatg aagacaaaata cttccaagga    6300 gttaaaaatg gcaatggaga ggtcctttaa tccagtcaac ctttacctg actgtggtgt    6360 aaaagaaaat gaggacgccc ttcctcctcc atctcccct cctcctcctc cttccaatgc    6420
gtcatctgaa attgaattc ctctccctcc tccaccacct ataatgctgt tgcctgaaaa    6480
aaatgagttt cctcctcat cacccacaga gaagtcaagg gctgaacttg agagcctccc    6540
aaccctgcct cttcctccac caccaggaga tgagaaatct gatcaggaat gtctaccaac    6600
atccctacct cctccccctc ccacagctcc atcccaacca gcacatcttc tttcctcctc    6660
tgttttagaa catcacagtg aagcatttt acaacagtat tcccgaaaag aaaccttgga    6720
ctctcatcag cttcactcac aggctaaaat cctaacagga aaatcaccac ccccaacact    6780
ccccaaaccc aaacttcccg agagaatcaa agctaagatg agccaggatt caccaagcgg    6840
```

```
tgaattggaa agatctctgt cagatgtgga aattaaaact accctctcaa aggatcagaa    6900
aagttcgctg gtggcagaaa gccgtgagca cacagaggcc aagcaagaag tattccgaaa    6960
aagccttgga agaaaacagc tgtcaattag ctctgcaaac tccctctctc agacagttcc    7020
agaaatccca gcacccaagg aaaaacagac agcaccccct gttaaatctc actcattccc    7080
atcaggttca gaacaacaaa gtcctaagcc ttacatgaga aaatttaaga cacccttaat    7140
gattgcggaa gaaaaataca gacagcaaag ggaagagctt gagaaacaga gacgggagag    7200
ttcttgccat agcatcatca aaacagaaac ccagcaccgc agcttatcag agaaagagaa    7260
agaaacagag ttacaaaaag cagctgaggc aatgtccact cccagaaagg attcagactt    7320
cactagggca cagcccaacc tggaacctaa aagcaaggct gtgatcgcca gtgaatgctc    7380
tgaaagccag ctctctacag cttccgcatt gacagtcgct accgagaggc tccagcatgt    7440
tctagccgct tcagacgata agcttaccct gcgacgggaa ggcacacaga actcaagtga    7500
caccctacaa tcgaaaacag cttgtgagat taaccagagt cacaaggaat gtaggacaga    7560
gcaaacattt gagcaacacg tggagaagtt gcccttcccc caaaccaaac ccatttcccc    7620
gagtttcaaa gtgaaaacta tcaggcttcc agctctagat catacgctga ctgaaacaga    7680
tctcagttct gaacgccgcg taaagcaatc cgaaattgac gttcaaacca gtactaaaga    7740
aatgaataag gaaattaaga aaaccgaagt gagcacacag tgtgataata agcaatctgt    7800
ggctgaaaaa tattttcaat tacctaaaac agagaaacgg gtgacggtac aaatgcccaa    7860
agactatgca gcgaaaagtc atcaaagcaa actccaaaca gttcccaaga agcatggagg    7920
attgggggag tttgacagag ggaatgtcct ggggagggaa ggaaaaaatc aggactcctc    7980
catgagcagt acaaaagaaa gcagggtaat agttgaaaga aagcaagaac atctacagga    8040
ccagagcgta ccaaggttag tccaacaaaa gattatcggt gaaagcctgg actcacgggt    8100
tcagaatttt cagcagacac aaacacaaac ttctaggatt gagcataaag aactgtccca    8160
accttacagt gagaaaaaat gtcttagaga caaggacaaa caacaaaaac aggtctcctc    8220
taacactgac gattcaaagc aagagataac acaaaaacaa tcttcatttt cctctgtgag    8280
agaatcccag caggatggag aaaaatgtgc cataaatata ttggaattct tgagaaaacg    8340
tgaagaacta cagcagattt tgtctagggt aaaacagttt gaagcagatt caaataaaag    8400
tggccttaaa acatttcaga cactgttaaa tattgctccg gtgtggctga taagtgagga    8460
gaaaagagaa tatggagttc gtgttgccat ggagaataat ttagaaaaag tcaaagaaga    8520
aataatacat attaaaactc aagcggagga gatgatcgtt cactgtgaac acgtaattcg    8580
aacagccatg atggcttccc aaacaggaaa gcagaaagat aaacctacca atcttaatga    8640
aatgccactg aaagtgtcta atgttaatct cagctctcat aaaggcactg aacagaaaga    8700
aagtaaaatt gtagaagaaa aattagcatc ccgccaagta gcaacccatt ctgaggcagc    8760
aactcataat cctgctaaaa catatcagga ggctaagggg gacgatagta agatggctcc    8820
tccctctttg aaaactcgcc caccatcacc aactttcatc accatcgaat ccactgcccg    8880
ccgagcagaa acatccacta agagtgagct ttctcagtcc cctaaaaata acagttgtgt    8940
tgaacctcta cccagaagac ccatggagca tacatctagg cttcccagaa caagtacatc    9000
accttcccca ccaaggagtc gttcagaaca acttgtcaga ctcaaagaca ccacggccag    9060
gttagccaaa ggcactatcc cttgttcacc aggaaccccg gttccagttg tcgagaagag    9120
atctgaagtt gtcatgtctc cagccacact ccgcaggcaa atcaagatag aaagccgtgg    9180
cggggactcc ccacccacca tcacaatacc tgtgagtgta aaccaccatg tcgtcagtgg    9240
```

```
ttccttcaga gaatcagtag acgctcaaga ggcagtgaag aaaacagaaa aaacagagac   9300
gtacgttcat aaagacaaaa agaattctgt cagtagcgca atgccagaga ctgaaagcta   9360
tgacgcagtt gaaatcatcc gcaaggtgga agggccccac ctatcagaac acagggagag   9420
atttgaagcc accaatcaaa ctgttcaaat ggctgaacat tttctgaatg ccacgaaaa    9480
tgaagtaaac agatggttta gggaatttga gaatggccca gttttcggag caaagacaga   9540
gagaagagct tatgcaaatg gcgaaataaa ccacaacatg aaacaagaga gtcatacgtt   9600
ttgcaaggag gaatttggat tagaatcttc tgaaactgct aattttacag gcttttctta   9660
cagacatcct agagagcatc gagcaaaagc ccctgcaacg cagcccaggg ttcactctga   9720
agccagagct ctcaatgagc attttttgag cgtggatgcg ttcgacagtc agattgtaga   9780
gtcacaggta gcaacctcat catcacggag ctcagaggca ggcagatctg gatttgattt   9840
taagcatgcc ccaccgacct atgaagatgt catcgctggc cacatcctag atattgcaga   9900
ttcgcctaca aacctcagac ggaattttca aaagacatgg caggagagtg aaagagtttt   9960
taagagcgtg ggatatgaaa cctcggatgc acatgcgaca gaaatgagca gggccttcca  10020
ggaggaattg gccttttttga gtgaaactgt tggtccaaga caaggaaatc tgcataattt  10080
gtcaaaagac ggtttatcca atggagtgcc tcgtagcaga ccagcagaat tttcataaat  10140
cttgcttcag atgccaccat tgcagcagta aactgagttt gggaaattac gcatcacttc  10200
acggacaaat atactgcaag cctcacttta aacaacttt caagtctaaa ggaaattatg   10260
atgaaggttt tggacacaag caacataaag accggtggaa ttgcaaaaac caaagcagct  10320
tagttgattc tattcccagc ggagagcccg atgctcggga aaaccctaca gcagatatcc  10380
tcttgcttgg ggatcttgct gtacatgcag acgcttgtaa cagcaagcgg caagacaatg  10440
gtttgagaaa atgggggggag aggggggaaat taaaaattgt ttggcctccc tgtcaggaga  10500
tgcctaagaa aaactctccc cctgaggaag aactcaaagt gaataaagct aaatggccac  10560
ctgagttgac catccctgtt ccctcagaat ttaaaggga gtcactgacc gaacacgtga    10620
aaatgttgga gagtcagggg caagaacaag atcacctccc tgaattgcaa ccctgccaac  10680
gcatttgtca gaaagaggac attacaggca tcaaagaaat aaaagggtac gaagaaagaa  10740
atgatgagaa agaagcaaag ggaaaggcgc aggatacgct gaaagatgca gagggcttga  10800
ggagtaagag aaaaagtggg atggagctta acgaccataa tgcgcatgct cagagtgatg  10860
gaaaggaaaa gaatgctcgt gctaatgaac ctgacagtgc agacatttta caagttacaa  10920
acaccgatga tgacgatgag gtgggggccag aaaatcatag ggagaacttc aataacaata  10980
acaataacaa ttctgtagct gtctcatcct gaataatgg caggcagcag acatctattt    11040
cagaatatcc tcatgtacta cagacagcca gtgaagcaaa ctattacaca aatgaatacc  11100
aaattaaaaa gtttaacaat gcctctagaa tctcagagtt actgggtata tttgagtctc  11160
aaaagtcgtc ctccaagaat gtcctagcct tggctctgga gagcacggct gacagaggga  11220
ctgcaggcag tcccatgcag ctggcactgg agcccggctt ccagcagggc ttatcagtta  11280
aaggggaaag ccttgcagtc tctaacgaag taaaccccct acacattaaa ggaaaccatg  11340
aaaataacaa gaatgtacac ctttttcttct ctaacactgt gaaaatcact tctttttcca  11400
agaaacataa catccttggg tgtgatttaa tagattctgt tgatcaactt aaaaatatgt  11460
catgcttgta tttaagagaa ctcgggaaaa atgtcaaatg ctggcatggt gaaactgcag  11520
gagcggctcg gcatggtgga aaaatgtgtt ttgatgctca gagccaagag agtgcggcta  11580
```

-continued

```
agcctgtgtt tcccagcatg cagtgccagg ctcaacatct gactgtggaa gagcagatta    11640
aacgggacag gtgctacagc gacagtgagg ctgactgaaa agtctttggc cacttgcagt    11700
tcatgctcgg gcactgaggg agcctgttct cggagaagac ctcgggatca tcgctaacct    11760
tttgatgagt ttgtaaagat cacgtttcat aatctcacca ttcacagcac attatttctt    11820
gtatcgcact ccataatcct tttccaccat tcacttgaga ctagtttgga tcttaatgaa    11880
atgctgagat gaaacatggt gaccgtgttt tcttctcaaa tggcgcatgg gctacggttt    11940
tctgtatctt aaagtgggag agagtctgca ccgctggtgt tcatcgccac tcttatacct    12000
tctctatatt ttctgatgaa ataaaatttt gtcaactgag atgcaaaaaa aaaaaaaaaa    12060
aaaaaaaaaa aaaaaaaaaa aaaaaaaaaa aaaaaaaaaa aaaaaaaaaa aaaaaaaaaa    12120
aaaaaaaaaa aaaaaaaaaa aaaaaaaaaa aaaaaaaaaa aaaaaaaaaa aaaaaaaa      12178
```

ACTIN RELATED CYTOSKELETAL PROTEIN "LACS"

The present application is a U.S. national phase filing under 35 U.S.C. § 371 of PCT/JP03/03613, filed on Mar. 25, 2003, which claims priority to JP Appl. No. 2002-255442, filed Aug. 30, 2002; the entire disclosures of each of which are hereby incorporated herein by reference for all purposes.

TECHNICAL FIELD

The present invention relates to novel actin-related cytoskeletal proteins, and genes encoding the proteins. Furthermore, the present invention relates to inventions utilizing the proteins and genes of this invention, such as pharmaceuticals comprising the proteins or genes as active ingredients.

BACKGROUND ART

Nitric oxide (NO) (Moncada and Higgs, Eur. J. Clin. Invest. 21 (4): 361-74 (1991)) is a messenger molecule that takes on various physiological roles in the cardiovascular, nervous, and immune systems (Griffith et al., J. Am. Coll. Cardiol 12: 797-806 (1998)). NO is produced together with L-citrulline from vascular endothelial cells, using arginine as a substrate and two types of nitric oxide synthases (NOSs; cNOS (constitutive) and iNOS (inductive); Bredt and Snyder, Proc. Natl. Acad. Sci. USA 87: 682-5 (1990); Janssens et al., J. Biol. Chem. 267: 22964 (1992); Lyons et al., J. Biol. Chem. 267: 6370-4 (1992)). Reports show that NO is involved in: (1) vasodilation mediated by vascular endothelial cells (Tanner et al., Circulation 83: 2012-20 (1991)); (2) inhibition of vascular intimal thickening (Garg and Hassid, J. Clin. Invest. 83: 1774-7 (1989)); (3) mediation of vasodilation in nonadrenergic noncholinergic nerves; (4) nerve cell death; (5) action as a neurotransmitter; (6) long-term potentiation and long-term depression of memory; (7) bactericidal effect of macrophages and neutrophils; (8) release of insulin from pancreatic β-cells (Life Science 49: L213-7 (1991)); (9) carcinogenesis (Gastoloenterology 103: 1260-6 (1992)); (10) antiplatelet effect (Radomski et al., Proc. Natl. Acad. Sci. USA 87: 5193-7 (1990)); and such. NO also has various antiarteriosclerotic and cardioprotective functions in the cardiovascular system. Thus, administration of NO synthase inhibitors causes cardiovascular remodeling such as inflammatory and proliferative changes in the cardiovascular tissues, thickening of the tunica media, perivascular fibrosis, and cardiomegaly.

L-NAME ($N^G$-Nitro-L-arginine methyl ester, hydrochloride) is a widely used NO synthase inhibitor that inhibits cNOS and iNOS. Continuous administration of L-NAME to rats can produce rats with inhibited NO production. In such model rats, increase of blood pressure as well as cardiovascular inflammatory and proliferative changes (infiltration of monocytes/macrophages, increase of MCP-1, elevation of NF-κB activity, etc.) occur within one week of L-NAME administration, and cardiovascular remodeling is observed from the fourth week onwards. Eventually, the rats die due to cardiac failure, renal failure, cerebral infarction, or such. Inflammatory and proliferative changes and arteriosclerotic lesions (pathologic changes) in rats with inhibited NO production are known to disappear when the effects of angiotensin II (AngII) or MCP-1 are suppressed.

Rho is a low-molecular-weight G protein that regulates the adhesion of cells to the extracellular matrix and vascular endothelium, and is involved in various processes including cell-substrate adhesion, cell migration, neurite retraction, cytokinesis, and cell cycle progression from $G_1$ to S phase. Many of these effects are due to the rearrangement of the actin cytoskeleton. The actin cytoskeleton is modulated by using Rho-regulated adhesion as a supporting point, and it enables the migration of cells into tissues and passing of cells through intercellular space. Rho is inactive in the GDP-bound form, and becomes active upon GTP binding. The activated GTP-bound Rho acts on effector molecules that are further downstream in the pathway. Rho-associated kinase (Rho-associated coiled-coil-forming protein kinase; ROCK) is a protein kinase and one of the Rho downstream effectors. Rho induction of the actin cytoskeleton occurs at different locations in the cell cycle to produce different skeletons of specific forms.

ROCK is a serine/threonine kinase having a molecular weight of 160 kDa. It has a kinase domain at the N terminus, a coiled-coil-forming region in the middle, and a membrane-bound domain at the C terminus. Previous analyses have shown that ROCK regulates the actin skeleton through a number of pathways (M. Maekawa et al., Science 285: 895-8 (1999)). In one of the pathways, myosin phosphatase is inactivated, and myosin is activated by directly phosphorylating the myosin light chain to induce actomyosin contraction. Another pathway involves the activation of LIM kinase. Activated LIM kinase becomes inactive upon phosphorylation of the actin-binding protein cofilin. As a result, the actin depolymerization activity of cofilin is suppressed, increasing filamentous actin. Yet another pathway involves phosphoactivation of $Na^+/H^+$ exchanger isoform-1. Upon activation, the exchanger promotes binding of the ERM (Ezrin/Radixin/Moesin) protein, and induces the binding of actin to cell membrane. ROCK is considered to contribute to the formation of cell membrane-bound actomyosin bundles through such pathways.

DISCLOSURE OF THE INVENTION

The present inventors have reported that NO-mediated changes in cardiovascular remodeling can occur due to a local increase of angiotensin convertase (ACE) activity in cardiac tissues, and can be suppressed almost completely by ACE inhibitors and angiotensin II receptor (AT1R) antagonists. However, many facts still remain unclear such as the mechanism of local activation of the renin-angiotensin system (RAS), the mechanism involved in the changes of cardiovascular architecture following signaling, etc. Thus, identification of genes that play important roles in the development of cardiovascular lesions (pathologic changes) is desired. Such genes and proteins encoded by these genes are also considered to be important in terms of the prevention and treatment of cardiac diseases.

The present inventors aimed to isolate and identify novel genes with important roles in the development of cardiovascular lesions. Therefore, the inventors initially focused on genes showing enhanced expression at sites of cardiovascular lesion, and especially aimed to isolate genes with locally enhanced expression in the heart by using the subtraction method (see Swaroop et al., Nucleic Acids Res. 19: 1954 (1991)). As a result, a novel gene of approximately 12-kb in full length, whose expression is increased in the heart following the administration of the L-NAME NO synthase inhibitor was isolated by screening a cDNA library. The novel gene obtained was named the LACS (L-NAME-related actin cytoskeletal protein) gene. Northern blot analysis showed that this gene is expressed in the heart and skeletal muscles. A particularly strong mRNA expression was confirmed in myocardial cells of the heart. Cellular distribution showed co-localization and expression with some of the actin stress fibers. Immunoprecipitation analysis showed that the expressed protein binds (directly or indirectly) to actin fibers, and Western blotting also showed it to be in the skeletal fraction. Furthermore, the amino acid sequence predicted from the nucleotide sequence of this gene was analyzed for its functions, properties, and such, and no characteristic sequences including signal sequences and transmembrane regions were found. However, a proline-rich sequence was present in the C terminus, and this sequence was found to be homologous to an SH3-binding domain.

The above-mentioned results, along with the large size of the gene and so on, indicated that LACS is a structural protein related to the cytoskeleton. LACS mRNA was abundantly expressed in a blood-pressure independent manner in the hearts of several model animals with hypertension and cardiomegaly (L-NAME rats, AngII infusion rats, and spontaneously hypertensive rats (SHRs)). In cultured myocardial cells, increased LACS mRNA expression due to hypertrophic agonist stimulation was observed. Furthermore, the expression mechanism was suggested to involve the AngII-AT1R pathway and the Rho/ROCK system. LACS was thought to increase in expression along actin upon hypertrophic stimuli, bind directly or indirectly to actin, and participate in the reorganization of actin fibers through functional modulation of actin. The above-mentioned increase of mRNA expression by angiotensin (AngII), phenylephrine, endothelin-1, and such suggests that at least a portion of LACS expression is regulated by the downstream signaling of the G-protein-coupled receptor.

This gene, which is highly expressed in hypertension and cardiomegaly model animals, has increased expression in cultured myocardial cells due to hypertrophic agonist stimulation, and encodes a protein that was suggested to associate with the modulation of actin polymerization, is expected to be used as a pharmaceutical for cardiac diseases such as cardiac failure, cardiomegaly, myocarditis, cardiomyopathy, arteriosclerosis, arteriosclerosis obliterans, or ischemic heart disease.

Accordingly, the present invention provides:

(1) A protein selected from (a) to (d):

(a) a protein comprising the amino acid sequence of SEQ ID NO: 1;

(b) a protein comprising the amino acid sequence of SEQ ID NO: 1, wherein one or more amino acids have been modified by deletion, substitution, addition, and/or insertion;

(c) a protein comprising a polypeptide encoded by a polynucleotide that hybridizes under stringent conditions with a polynucleotide comprising the nucleotide sequence of SEQ ID NO: 2; and (d) a protein comprising an amino acid sequence having 60% homology to the amino acid sequence of SEQ ID NO: 1;

(2) A polynucleotide encoding the protein of claim 1 or a portion thereof;

(3) The polynucleotide of claim 2, which comprises the nucleotide sequence of SEQ ID NO: 2;

(4) A pharmaceutical comprising the protein of claim 1;

(5) The pharmaceutical of claim 4, which is used to prevent, improve, or treat cardiac failure, cardiomegaly, myocarditis, cardiomyopathy, arteriosclerosis, arteriosclerosis obliterans, or ischemic heart disease;

(6) A pharmaceutical comprising the polynucleotide of claim 2; and (7) The pharmaceutical of claim 6, which is used to prevent, improve, or treat cardiac failure, cardiomegaly, myocarditis, cardiomyopathy, arteriosclerosis, arteriosclerosis obliterans, or ischemic heart disease.

The present invention provides the novel gene LACS, which plays an important role in cardiovascular lesions. The nucleotide sequence of the LACS cDNA is shown in SEQ ID NO: 2, the amino acid sequence of the LACS protein predicted from the nucleotide sequence and encoded by the LACS cDNA is shown in SEQ ID NO: 1.

The proteins of this invention are proteins comprising the amino acid sequence of SEQ ID NO: 1. These proteins can be obtained, for example, from cells producing these proteins using an affinity chromatography column to which antibodies against the protein are bound. The proteins can also be purified by conventional protein purification techniques based on the molecular weight of the LACS protein (373 kDa) and their binding affinity to actin. Since the expression of LACS protein in cultured myocardial cells can be induced by L-NAME administration, L-NAME-induced LACS protein can be isolated and purified by: salting out; chromatography such as gel filtration chromatography, ion-exchange chromatography, reverse-phase chromatography, affinity chromatography, hydrophobic chromatography, adsorption chromatography, and such; gel electrophoresis; ultrafiltration; re-crystallization; distillation; dialysis; isoelectric focusing; filtration; immunoprecipitation; solvent extraction; solvent precipitation; and such (see, ed. Marshak et al., Strategies for Protein Purification and Characterization: A Laboratory Course Manual, Cold Spring Harbor Press (1996)).

Fusion proteins are included in the proteins comprising the amino acid sequence of SEQ ID NO: 1. Examples of such fusion proteins are: the proteins of this invention to which a signal sequence instructing host cells to secrete is added for easy purification, when the proteins are expressed by genetic engineering techniques; and those attached with a tag comprising FLAT, histidine residues, or such for easy recovery, or a tag such as GFP for detection. Fusion proteins cleavable by thrombin, Xa factor, or such using conventional techniques can be prepared, and portions other than the portions corresponding to the proteins of this invention can be deleted as necessary.

The proteins of this invention can also be proteins comprising an amino acid sequence obtained by modifying the amino acid sequence of SEQ ID NO: 1, through deletion, substitution, addition, and insertion of one or more amino acids. Such proteins can be obtained by modifying and expressing the polynucleotides encoding proteins comprising the amino acid sequence of SEQ ID NO: 1 by commonly used genetic techniques. Genetic modification techniques include, for example, the site-directed mutagenesis method (ed. Ausubel et al., Current Protocols in Molecular Biology, publish. John Wiley & Sons, section 8.1-8.5 (1987)). Such modified proteins can also be used to prepare fusion proteins as described above, as necessary.

Furthermore, the proteins of this invention are proteins comprising a polypeptide encoded by a polynucleotide that hybridizes under stringent conditions with a polynucleotide comprising the nucleotide sequence of SEQ ID NO: 2. Such proteins can be obtained by, for example, preparing probes based on the nucleotide sequence of SEQ ID NO: 2, screening a mammalian cDNA library, genomic library, and such by the hybridization method (ed. Ausubel et al., Current Protocols in Molecular Biology, publish. John Wiley &

Sons, section 6.3-6.4 (1987)), and expressing the obtained polynucleotides. However, the phrase "polynucleotide that hybridizes under stringent conditions with the polynucleotide comprising the nucleotide sequence of SEQ ID NO: 2" as used in this invention is not intended to restrict such polynucleotides to those obtained by the hybridization method. Therefore, polynucleotides that can be produced by techniques such as the aforementioned site-directed mutagenesis are included in the definition, as long as they hybridize under stringent conditions with the nucleotide sequence of SEQ ID NO: 2. Herein, the term "stringent conditions" refers to conditions of low salt concentration or high temperature in the washing step, and includes conditions of 1×SSC, 0.1% SDS, 370° C. (or 55° C.).

The proteins of this invention include proteins comprising an amino acid sequence homology of 50% or more, preferably 70% or more, more preferably 80% or more, even more preferably 90% or more, and most preferably 95% or more (for example, 96%, 97%, 98%, 99%, or more) to the amino acid sequence of SEQ ID NO: 1. Such proteins can be obtained by the above-mentioned site-directed mutagenesis and hybridization method, PCR method (ed. Ausubel et al., Current Protocols in Molecular Biology, publish. John Wiley & Sons, section 6.1-6.4 (1987)), and such. The homologies in this invention are determined using the BLAST algorithm (Karlin and Altschul, Proc. Natl. Acad. Sci. USA 90: 5873-7 (1993)). Programs such as BLASTX (Altschul et al., J. Mol. Biol. 215: 403-10 (1990)) that have been developed based on the BLAST algorithm are known. One can refer to www.ncbi.nlm.nih.gov for the specific analytical procedures.

The LACS protein of this invention is highly expressed in the hearts of several hypertension and cardiomegaly model animals, and is encoded by a gene whose expression increases locally in the heart upon administration of the L-NAME NO synthase inhibitor. Therefore, the protein expression can be used as a basis for detecting the inhibition of NOS expression or activity, and enables the diagnosis of diseases induced by decreased NOS expression or activity. Detection of the protein expression is not limited thereto, and can be done using antibodies against the protein. An Antibody against a protein of this invention can be produced by conventional techniques using apparently the protein comprising the amino acid sequence of SEQ ID NO: 1, or a portion thereof, or using an above-mentioned protein of this invention that has the antigenicity of the protein comprising the amino acid sequence of SEQ ID NO: 1. Therefore, the proteins of this invention and peptide fragments thereof can be used to produce antibodies that enable the diagnosis of diseases induced by decreased NOS expression or activity. When the proteins of this invention are used as pharmaceuticals for humans, human-derived LACS protein is preferably used, but is not limited thereto. Human-derived LACS protein can be obtained by generating probes or primers based on the sequence information of the LACS protein and gene of this invention, obtaining a gene encoding the desired protein using the above-mentioned hybridization method or various PCR methods, and expressing this gene.

The proteins of this invention include proteins that are functionally equivalent to the proteins comprising the amino acid sequence of SEQ ID NO: 1. Herein, the phrase "functionally equivalent to the proteins comprising the amino acid sequence of SEQ ID NO: 1" refers to having the activity to enhance or suppress the polymerization, crosslinking, or bundle formation of actin. Proteins functionally equivalent to the LACS protein comprising the amino acid sequence of SEQ ID NO: 1 also include proteins that can be obtained by using the above-mentioned site-directed mutagenesis method, hybridization method, PCR method, and such.

Furthermore, the present invention provides polynucleotides that encode the proteins of this invention, or portions thereof. Such polynucleotides include cDNAs, genomic DNAs, mRNAs, and chemically synthesized DNAs and RNAs. A single protein of the present invention can be encoded by a plurality of polynucleotides due to the degeneracy of the genetic code. Thus, the polynucleotides of this invention also include such degenerate polynucleotides. Naturally occurring polynucleotides of this invention can be obtained by, for example, generating probes, primers, and such based on the entire or a portion of the nucleotide sequence encoding the LACS protein of this invention comprising SEQ ID NO: 2, and performing well-known techniques such as hybridization and PCR. Furthermore, if necessary, the obtained polynucleotides can be modified by, for example, restriction enzyme digestion, site-directed mutagenesis, or addition of a suitable fragment (including linkers, initiation codons and stop codons), linked to a polynucleotide encoding a different polypeptide for fusion protein expression, or integrated into an appropriate vector (expression vectors, cloning vectors, and such). The polynucleotides of this invention also include these polynucleotides.

The present invention also provides polynucleotides comprising at least 13 consecutive nucleotides complementary to the nucleotide sequence of SEQ ID NO: 2 or its complementary strand. Such complementary polynucleotides do not have to be completely complementary to the nucleotide sequence of SEQ ID NO: 2 or its complementary strand, as long as they have homologies of at least 70% or higher, preferably 80% or higher, more preferably 90% or higher, and even more preferably 95% or higher. Homology can be determined according to the aforementioned methods. Such polynucleotides can be used as probes or primers for the detection and amplification of DNAs and mRNAs encoding the proteins of this invention. When the polynucleotides are used as primers, restriction enzyme recognition sequences and/or tags, for example, can be added to their 5' ends as necessary. The polynucleotides may also be used as antisense nucleotide sequences, ribozymes, and such. Antisense nucleotide sequences and ribozymes can be used for inhibiting or suppressing the expression of the proteins of this invention.

The proteins of this invention can be obtained by integrating the polynucleotides of this invention into appropriate expression vectors under the control of an expression regulatory region comprising enhancers, promoters, and such, and introducing the vectors into appropriate host cells. Examples of the host cells are prokaryotic cells and eukaryotic cells. For eukaryotic cells, systems using *E. coli* are well known. Examples of the promoters used when the host is *E. coli* are lacZ promoter (Ward et al., Nature 341: 544-6 (1998)), and ara promoter (Better et al., Science 240: 1041-3 (1988)). When *E. coli* is used as a host to produce the proteins of this invention by genetic engineering methods, attachment of a signal sequence that enables the production of proteins into the periplasm is desired for easy purification. An example of the signal sequence is pelB signal sequence (Lei et al., J. Bacteriol. 169: 4379 (1987)). The expression vectors for *E. coli* may further include the replication origins derived from SV40, polyomavirus, adenovirus, bovine papilomavirus, and such, and selection markers such as aminoglycoside transferase gene, thymidine kinase gene, xanthine guanine phosphoribosyl transferase gene, and dihydrofolate reductase gene. In addition to *E. coli*, prokaryotic expression systems using *Bacillus subtilis* as the host are well known.

For eukaryotic hosts, yeast cell systems, plant cell systems, and animal cell systems including insect cells, amphibian cells, and mammalian cells are known. Generally used yeast cell systems include systems that use a *Saccharomyces* yeast or an *Aspergillus* mold as host. For plant cell systems, those that use *Nicotiana tabacum* cells as hosts are known. In plant cell systems, proteins can be produced in callus cultures, or obtained by regenerating plants from cells transfected with the desired gene and obtaining the proteins of interest from the leaves, roots, stems, and such of the plants (Julian et al., Eur. J. Immunol. 23: 131-8 (1994)). Examples of the mammalian cells include BHK, CHO, COS, HeLa, myeloma, and 3T3. Xenopus oocytes (alle et al., Nature 291: 358-40 (1981)) are known as amphibian cells while Sf9, Sf21, Tn5, and such are well-known insect cells. The constructed vectors are introduced into host cells by well-known methods such as the calcium phosphate method (Virology 52: 456-67 (1973)), and electroporation method (EMBO J. 1: 841-5 (1982)).

The proteins of this invention can also be produced in vivo using animals (see Lubon, Biotechnol. Annu. Rev. 4: 1-54 (1998)). Examples of the animals are: domestic animals such as cattle, sheep, pigs, and goats (Ebert et al., Bio/Technology 12: 699-702 (1994)); mammals such as mice; insects such as silkworms. For the production of an exogenous protein in mammals, a DNA encoding the protein of interest is fused with a gene encoding a protein specifically secreted in milk, such as β-casein. Next, the fusion gene is injected into the embryo of the animal to induce chromosomal recombination. The protein of interest can be obtained from the milk produced by the transgenic animals (i.e., those born as a result of transplanting this embryo transplanted into the uterus of a female animal) or from their offspring. Alternatively, when silkworms are used, baculovirus that carries an integrated gene encoding the desired protein is used to infect silkworms, and the desired protein can be obtained from the silkworm body fluids (Susumu et al., Nature 315: 592-4 (1985)).

Proteins that have been secreted inside or from host cells as a result of genetic engineering can be purified by the same method as for the naturally occurring proteins. For proteins that have been optionally modified for the convenience of purification, the modified peptide portions can be removed by reacting with an appropriate protein modification enzyme before or after protein purification.

Antibodies against the proteins of this invention can be obtained using the proteins of this invention, or portions thereof. The antibodies in this description include polyclonal antibodies, monoclonal antibodies (Milstein et al., Nature 305: 53740 (1983)), and antibody fragments. A polyclonal antibody against a protein of this invention may be, for example, serum obtained from the blood of a mammal sensitized with an antigenic portion of a protein of this invention. This serum can be further purified to prepare fractions comprising the polyclonal antibody. On the other hand, monoclonal antibodies can be prepared using the hybridoma method (Kohler and Milstein, Nature 256: 495 (1975)), by collecting immunocytes from mammals sensitized with an antigen; cloning hybridomas by fusing the collected cells with cells capable of permanent proliferation, such as myeloma cells; collecting monoclonal antibodies from the culture.

Antibody fragments refer to fragments comprising the antigen-binding region or variable region of an antibody, and include Fab, Fab', F(ab')2, and Fv fragments and such. Fab is a fragment obtained by papain digestion of antibody molecules. Pepsin digestion of an antibody yields the F(ab')2 fragment. As for other antibody fragments, examples include diabodies (Holliner et al., Proc. Natl. Acad. Sci. USA 90: 6444-8 (1993)), filamentous antibodies, single chain antibodies such as scFV (Plucktun, "The Pharmacology of Monoclonal Antibody", Vol. 113, ed. Rosenburg and Moore, Springer Verlag, pp. 269-315 (1994)), and multispecific antibodies (LeDoussal et al., Int. J. Cancer Suppl. 7: 58-62 (1992); Paulus, Behring Inst. Mitt. 78: 118-32 (1985); Millstein and Cuello, Nature 305: 537-9 (1983); Zimmermann, Rev. Physiol. Biochem. Pharmacol. 105: 176-260 (1986); Van Dijk et al., Int. J. Cancer 43: 944-9 (1989)). Furthermore, the antibodies of this invention can be modified by molecules such as polyethylene glycol. The antibodies thus obtained can be purified by methods similar to those for purifying other proteins (ed. Harlow and David Lane, Antibodies: A Laboratory Manual, Cold Spring Harbor Laboratory (1988)).

Since the proteins of this invention are expressed specifically in myocardial cells, and increase in diseased conditions such as left ventricular hypertrophy, they may be used to prevent, improve, or treat cardiac diseases such as cardiac failure, cardiomegaly, myocarditis, cardiomyopathy, arteriosclerosis, arteriosclerosis obliterans, or ischemic heart disease. Therefore, by enhancing or regulating the functions of the proteins of this invention, these proteins can be formulated as agents to prevent, improve, or treat these cardiac diseases. When the proteins are used as pharmaceuticals, they can be administered to a patient directly and on their own, or formulated using conventional formulation methods. Examples of such methods include dissolving into a neutral solution such as PBS. Furthermore, pharmaceutically acceptable stabilizers, buffers, sweeteners, diluents, corrigents, fillers, coloring agents, emulsifiers, excipients, disintegrating agents, flavoring agents, preservatives, solubilizers, and such may be added as necessary. By combining with carriers, the proteins of this invention can be prepared into forms such as solutions, elixirs, capsules, granules, pills, suspensions, powders, tablets, syrup, injections, troches, and emulsions.

The dosage of the pharmaceuticals comprising the proteins of this invention depends on a number of factors such as the weight, age, and symptoms of the patient, as well as the method and form of administration. One skilled in the art can determine the appropriate dosage. The pharmaceuticals can be, for example, administered subcutaneously or orally, or administered by intraarterial or intravenous injection. The daily protein dosage for adults (body weight of 60 kg) is normally 1 μg to 10 g, preferably 10 μg to 1 g, and more preferably 100 μg to 100 mg. Furthermore, the dosage can be calculated based on the body weight when administering into animals other than humans.

Instead of the proteins of this invention, polynucleotides encoding these proteins may be used as pharmaceuticals. Similarly to pharmaceuticals comprising the proteins of this invention, pharmaceuticals comprising such a gene as an active ingredient can be used to prevent, improve, or treat cardiac diseases such as cardiac failure, cardiomegaly, myocarditis, cardiomyopathy, arteriosclerosis, arteriosclerosis obliterans, or ischemic heart disease. Hereinafter, methods, forms, and amounts of gene transfer will be described specifically for gene therapies using the polynucleotides of this invention.

Methods for administering gene therapy agents comprising a LACS gene as an active ingredient can be classified into two groups: methods using non-viral vectors and methods using viral vectors. The preparation methods, administration methods, and such for these vectors are described in detail in experiment manuals (Jikken Igaku (Experimental Medicine) Supplementary Volume, "Idenshichiryo no Kisogijyutsu (Fundamental Techniques for Gene Therapy)", Yodosha, 1996; Jikken Igaku (Experimental Medicine) Supplementary Volume, "Idenshidonyu & Hatsugenkaiseki Jikkenho (Experimental Methods for Gene Transfer & Expression Analysis)", Yodosha, 1997; "Idenshi-chiryo Kaihatsu Kenkyu Handbook (Handbook of Gene Therapy Research and Development)", Nihon Idenshichiryo Gakkai (The Japan Society of Gene Therapy) Edition, NTS, 1999).

The target gene can be introduced into cells or tissues by using the methods below and a recombinant vector prepared by inserting a target gene into a conventional non-viral gene expression vector. Examples of methods for transferring genes into cells are: lipofection methods, calcium-phosphate co-precipitation methods, DEAE-dextran methods, methods that directly infuse DNA using a glass capillary tube, etc. Methods for transferring genes into tissues include methods using virus envelope vectors, internal type liposomes, electrostatic type liposomes, HVJ-liposomes, improved type HVJ-liposomes (HVJ-AVE liposomes), receptor-mediated gene transfer methods, methods for transferring carriers (such as metal particles) along with DNAs using particle guns, methods for directly introducing naked-DNAs, introduction methods using positively charged polymers, etc.

The aforementioned HVJ-liposomes are constructed by incorporating a DNA into a liposome formed by a lipid bilayer, then fusing this liposome with an inactivated Sendai virus (hemagglutinating virus of Japan; HVJ). The use of HVJ-liposomes is characterized by extremely high cell membrane fusion compared to conventional liposome methods, and is one of the especially preferred forms of introduction. Methods for preparing HVJ-liposomes are described in detail in, for example, Experimental Medicine Supplementary Volume, "Idenshichiryo no Kisogijyutsu (Fundamental Techniques of Gene Therapy)", Yodosha, 1996; Experimental Medicine Supplementary Volume, "Idenshidonyu & Hatsugenkaiseki Jikkenho (Experimental Methods for Gene Transfer & Expression Analysis)", Yodosha (1997); J. Clin. Invest. 93: 1458-64 (1994); Am. J. Physiol. 271: R1212-20 (1996). Methods for using the HVJ-liposome are described in, for example, Molecular Medicine 30: 1440-8 (1993); Jikken Igaku (Experimental Medicine), 12: 1822-6 (1994); and Tanpakushitsu Kakusan Kouso (Protein, Nucleic Acid, and Enzyme), 42: 1806-13 (1997); and a more preferable method is described in Circulation 92 (Suppl. II): 479-82 (1995).

Furthermore, methods using viral envelopes are particularly preferable when administering a LACS gene of this invention. Viral envelopes can be prepared by mixing a purified virus with an expression vector of interest in the presence of a surfactant, or by freezing and thawing a mixture of a virus and an expression vector (JP-A 2001-286282).

The viruses that can be used in the viral envelope methods are viruses belonging to families such as the retrovirus, togavirus, coronavirus, flavivirus, paramyxovirus, orthomyxovirus, bunyavirus, rhabdovirus, poxvirus, herpesvirus, baculovirus, and hepadnavirus families, and HVJs are particularly preferable. Herein, these viruses can be either wild-type or recombinant viruses. In particular, a recombinant HVJ reported by Hasan, M. K. et al. (J. General Virol. 78: 2813-20 (1997)), Yonemitsu, Y. et al. (Nature Biotech. 18: 970-3 (2000)), or such may be used as an HVJ.

While the Z strain (available from ATCC) of HVJ is generally preferable in methods using HVJ-liposomes or HVJ-envelopes, fundamentally, other HVJ strains (for example, ATCC VR-907 and ATCC VR-105) can also be used. When preparing a viral envelope, purified viruses can be inactivated by UV irradiation and such, and mixed with a desired expression vector. Surfactants that can be used for mixing the virus and expression vector include, for example, octylglucoside, Triton X-100, CHAPS, and NP-40. Viral envelope vectors prepared in this manner can be introduced by injection or such into tissues to be targeted for therapy, prevention, or remedy. Furthermore, by freezing at −20° C. the viral envelope vectors can be stored for at least two to three months.

Any expression vector may be used here as long as they can express a target gene in vivo. Examples of the expression vectors are pCAGGS (Gene 108: 193-200 (1991)), pBK-CMV, pcDNA3.1 (Invitrogen), and pZeoSV (Stratagene).

Representative methods for gene transfer with viral vectors are those methods using viral vectors such as recombinant adenoviruses and retroviruses. More specifically, a target gene can be transferred into cells by the steps of: introducing the gene into DNA or RNA viruses such as detoxicated retroviruses, adenoviruses, adeno-associated viruses, herpesviruses, lentiviruses, vaccinia viruses, poxviruses, polioviruses, sindbis viruses, Sendai viruses, SV40, or human immunodeficiency viruses (HIV) (see Pharmacol. Ther. 80: 35-47 (1998); Front. Biosci. 4: E26-33 (1999); J. Recep. Signal. Transduct. Res. 19: 673-86); and then infecting cells with the resultant recombinant virus. The infection efficiency of adenovirus vectors is much greater than the other aforementioned viral vectors. Thus, from this viewpoint, the use of an adenovirus vector system is preferred.

Methods for introducing an agent of the present invention to a patient during gene therapy include: the in vivo introduction of a gene therapy agent directly into the body; and the ex vivo introduction of a gene therapy agent into a cell harvested from the patient, followed by reintroduction of the modified cell into the body (Nikkei Science, April 1994, 20-45; Gekkann Yakuji 36 (1), 23-48, 1994; Jikken Igaku (Experimental Medicine) Supplementary Volume, 12 (15), 1994; "Idenshi-chiryo Kaihatsu Kenkyu Handbook (Handbook of Gene Therapy Research and Development)", Nihon Idenshichiryo Gakkai eds. (The Japan Society of Gene Therapy) Edition, NTS, 1999). In vivo methods are particularly preferred in the present invention.

Various formulations, (for example, liquid preparations), suited for each of the above-mentioned administration methods may be adopted as the form of preparation. For example, an injection comprising a gene as an active ingredient can be prepared by conventional methods, which might include dissolving a gene in an appropriate solvent (e.g., a buffer solution, such as PBS, physiological saline, and sterilized water), sterilizing by filtration as necessary, and then loading into a sterile container. Conventional carriers or such may be added to injection agents as required. Alternatively, liposome preparations, such as preparations comprising HVJ-liposome, can be prepared as suspensions, frozen agents, or centrifugally concentrated frozen agents.

The dosage of the pharmaceuticals comprising the polynucleotides of this invention depends on a number of factors such as the weight, age, and symptoms of the patients, as well as on the method and form of administration. One skilled in the art can determine the appropriate dose. The pharmaceuticals can be, for example, administered subcutaneously or orally, or by intraarterial or intravenous injection. The daily polynucleotide dosage for adults (body weight of 60 kg) is normally 1 µg to 10 g, preferably 10 µg to 1 g, and more preferably 100 µg to 100 mg. Furthermore, the dosage can be calculated based on the body weight when administering to animals other than humans.

More specifically, since the polynucleotides of this invention can be repeatedly administered when using the HVJ-envelope method, the gene is administered a number of times, for example, twice or three times, but not all together at once, in order to obtain better therapeutic, preventive, or improvement effects. The present invention also includes such types of administration which are performed over a number of times using the HVJ envelope.

The appropriate administration methods and sites to be administered for the pharmaceuticals comprising the proteins or polynucleotides of this invention are selected according to the disease and symptoms to be treated. The preferred administration method is intramyocardial or intramuscular administration, but is not limited thereto.

Since the LACS gene of this invention was found to increase in the heart of several hypertension and cardiomegaly model animals, it can be used to diagnose the presence or absence of hypertension and cardiomegaly in patients. Such diagnoses may be performed by detecting intracellular mRNAs transcribed from the gene, using probes or primers generated based on the sequence information of the LACS gene of this invention. Extraction of mRNAs from biological samples can be also performed using a commercially available kit (such as the mRNA Purification Kit (Pharmacia) and QuickPrep mRNA Purification Kit (Pharmacia)). In addition, methods for preparing total RNAs, such as guanidine ultracentrifugation methods (Chirgwin et al., Biochemistry 18: 5294-9 (1979)) and AGPC methods (Chomczynski and Sacchi, Anal. Biochem. 162: 156-9 (1987)), are well known. Meanwhile, methods for detecting proteins expressed from these genes using antibodies against the proteins of this invention may also be considered. When examining the indicator gene expression in cells, its expression level is usually corrected with the measured expression levels of genes whose expression levels do not vary substantially with the cellular condition (housekeeping genes such as β-actin and glyceraldehyde-3-phosphate dehydrogenase (GAPDH) are often used).

The LACS protein and the LACS gene of this invention can be used to screen for compounds useful as pharmaceuticals for cardiovascular diseases. As indicated in the present invention, in vivo expression of the LACS protein increases in response to the administration of NO synthetic inhibitors or hypertrophic agonists. Therefore, compounds that bind to the LACS protein may be candidates of pharmaceuticals for cardiovascular diseases. Such compounds can be screened, for example, by the steps of:

(1) contacting a test compound with a proteins of this invention or a partial peptide thereof;

(2) detecting the binding of the test compound to the protein, or partial peptide; and (3) selecting a test compound that binds to the protein, or the partial peptide.

Alternatively, binding of test compounds to proteins of this invention can be investigated by contacting test compounds with host cells that maintain the expression of polynucleotides encoding the proteins of this invention, or with a host cell culture, instead of the proteins of this invention or partial peptides thereof in step (1).

In the present invention, the LACS protein was shown to bind to actin. By regulating the binding between the LACS protein and actin, actin polymerization may be enhanced or suppressed. Therefore, compounds that inhibit the binding between the LACS protein and actin may be candidates of pharmaceuticals for cardiovascular diseases. Methods for screening compounds that inhibit the binding of the LACS protein can be performed using the binding between the protein and actin as an index. More specifically, such compounds can be screened, for example, by the steps of:

(1) contacting a test compound with a protein of this invention or a partial peptide thereof in the presence of actin;

(2) detecting the binding of actin to the protein or partial peptide; and (3) selecting a test compound that suppresses or inhibits the binding of actin to the protein or partial peptide.

The partial peptides used here must comprise the portion(s) involved in the binding between the LACS protein and actin. Such partial peptides can be obtained easily by analyzing the actin affinity of the various fragments produced upon digestion of the LACS protein. Furthermore, binding between the LACS protein and actin may be carried out by methods as described in Example 7, using LACS antibodies and actin antibodies, but is not limited thereto.

The present invention also provides methods of screening for compounds that regulate the expression of the proteins of this invention. Compounds that enhance or suppress the expression of the LACS protein may be candidates of pharmaceuticals for cardiovascular diseases. Such screening can be performed using myocardial cells and smooth muscle cells expressing the LACS gene by the steps of:

(1) contacting a test compound with cells expressing the LACS gene;

(2) detecting the expression of LACS gene; and (3) selecting a test compound that enhances or suppresses the expression of the LACS gene compared to when the test compound is absent.

Various cells including *E. coli*, yeast, insect cells, plant cells, oocytes, and mammalian cells can be used for the expression of the LACS gene. Similarly to the detection of the in vivo expression of LACS gene in patients, transcribed mRNAs and proteins can be detected according to conventional methods.

Furthermore, cells that have been transformed with an expression vector, in which a reporter gene is operably linked to an expression regulatory sequence upstream of the LACS gene, can be used in place of cells that express the LACS gene. Examples of the upstream expression regulatory sequence of the LACS gene are promoters, enhancers, CAAT box, and TATA box. For example, probes are generated based on the nucleotide sequence of SEQ ID NO: 2, and genomic DNA clones comprising the expression regulatory sequence of the LACS gene is obtained by screening a genomic DNA library. The expression regulatory sequence portion of this clone is excised by restriction enzyme treatment, and then cloned to be operably linked to the upstream of an appropriate reporter gene. Examples of the reporter gene are chloramphenicol acetyltransferase (CAT) gene, lacZ gene, luciferase gene, green fluorescent protein (GFP) gene, and growth hormone gene. The obtained construct in which a reporter gene is linked downstream of the LACS gene expression regulatory sequence is introduced into an appropriate host cell (preferably mammalian cells) by any one of the above-described methods. When this construct is intended for the insertion into the host cell chromosome, homologous recombination techniques may be used.

Expression of the reporter gene is detected by methods appropriate for the type of reporter gene employed. For example, the level of CAT gene expression is determined by the detection of chloramphenicol acetylation due to the gene expression product. When using the lacZ gene, the coloring catalysis of the coloring compound in the gene expression product is measured as an indicator of the expression level of the gene. When the reporter gene is the luciferase gene, fluorescence of a fluorescent compound that results from the catalysis of the gene expression product is detected and this can be used as an indicator of expression level. Since GFP protein emits fluorescence, when the GFP gene is used as the reporter gene, the expression level is determined according to the fluorescence level of the expression product. When using the growth hormone gene, the effects (growth stimulation, proliferative stimulation, and such) of the gene expression product on cells are examined and the expression level is quantified.

Examples of test compounds to be used in each of the above-mentioned screening methods include naturally occurring compounds, synthetic compounds, inorganic compounds, organic compounds, and proteins, peptides, and non-peptide compounds that are crude, purified or partially purified. In addition, compound libraries comprising a plurality of compounds, expression products derived from a gene library, cell extracts, cell culture supernatants, products of luminescent microorganisms, extracts of marine organisms, plant extracts, biological tissue extracts, and such may also be used. Proteins or peptides can be used as test compounds by binding with a carrier, fusing with another polypeptide, or expressing on a cell membrane and preparing membrane fractions. These test compounds can be labeled with radiolabeling, fluorescence labeling, and such, as necessary.

Cells, expression vectors, test compounds, probes, primers, antibodies, substrates for measuring reporter gene expression, and such, which are necessary for each of the above-mentioned screening methods, can be appropriately combined into kits. Furthermore, the kits may include, as necessary, media and containers for cell culturing, control samples, kit instructions, and such. Test compounds selected by the above-mentioned-screening can be made into pharmaceuticals to be used directly on patients by themselves, but they may also be formulated and used according to conventional formulation methods, as necessary. When the compounds are polynucleotides such as DNAs, or polypeptides that can be encoded by DNAs, the polynucleotides may be administered according to the aforementioned gene therapeutic methods.

BEST MODE FOR CARRYING OUT THE INVENTION

Hereinafter, the present invention will be specifically described using Examples, but it is not to be construed as being limited thereto.

EXAMPLE 1

Gene Isolation by Subtractive Hybridization (SSH)

RNAs were extracted from the hearts of a male WKY rat group that has been subjected to a one-week oral administration of L-NAME (100 mg/L), and from the hearts of a control group without L-NAME administration. The obtained RNAs were used to clone cDNAs that showed enhanced expression in the L-NAME-administered group using the subtraction method. As a result, a novel LACS (L-NAME related actin cytoskeletal protein) gene was successfully isolated. Northern blotting was used to analyze the mRNA expression of this gene in cardiac tissues, and showed that the expression level reaches its peak one to three days after L-NAME administration, begins declining from the seventh day, and gradually decreases to nearly the baseline 28 days after administration. Furthermore, mRNA expression in tissues other than the heart was also analyzed by Northern blotting. The LACS mRNA expression was observed in the heart and skeletal muscles. Particularly with the heart, the expression of LACS mRNA was confirmed in the myocardial cells.

EXAMPLE 2

Isolation of Full-length cDNA

A cDNA library was constructed, and a full-length cDNA encoding LACS was isolated by screening. More specifically, poly (A)$^+$ RNAs obtained from WKY rats on the first day of L-NAME administration were used to construct a λZAPII cDNA library using random primers. Next, by repeated screening using the LACS gene fragments as probes, an approximately 12-kb cDNA in full length was obtained as the LACS gene. Sequencing of this cDNA was performed using the ABI PRISM310 DNA Sequencer (ABI/Perkin Elmer). The obtained nucleotide sequence is shown in SEQ ID NO: 1. Characteristic sequences such as signal sequences or transmembrane regions could not be found in the amino acid sequence (SEQ ID NO: 2) predicted from the nucleotide sequence. Therefore, it was difficult to predict the properties and functions of LACS from the sequence alone. However, a proline-rich sequence exists at the C terminus of the predicted amino acid sequence, suggesting an SH3-binding domain homology. SH3 is a homologous portion of approximately 70 amino acids seen in the Src kinase family. The SH3-binding domain is a proline-rich sequence of approximately ten amino acids.

EXAMPLE 3 mRNA Expression in the Hearts of Hypertension Models

Cardiac tissues derived from AngII infusion rats (osmotic pump: 0.7 mg/kg/day), and SHRs of 4 weeks and 24 weeks, were used. ATIR antagonist (ARB) and hydrazine (Hyd) were used as antihypertensive agents. Each of the antihypertensive agents was used at an amount sufficient for lowering the blood pressure (10 mg/kg/day for ARB; 12 mg/kg/day for Hyd).

The results present a trend of increased LACS expression after the third day of AngII administration, and decreased expression after the seventh day in the AngII infusion rats. Most of this increase in expression tended to be suppressed by a simultaneous ARB administration, but not by the simultaneous administration of hydrazine. However in SHRs, a significant increase of LACS mRNA expression was observed in adult rats that had developed hypertension with progressing cardiomegaly, but not in juvenile rats that had not yet developed hypertension.

As described above, increase of LACS mRNA expression was observed in the hearts of several hypertension and cardiomegaly model animals, and even the correction of hypertension did not completely suppress this expression. These findings suggest the possibility that the LACS mRNA expression is amplified by local activation of the RAS system. Therefore, cellular response to AngII stimulation was examined in Example 6.

EXAMPLE 4

Localization of the LACS Protein

The C-terminal portion of LACS was used to prepare an antibody against LACS. Intracellular localization of LACS was examined by cellular staining using the peptide antibody.

(1) Localization in the Heart

LACS was stained in the cardiac tissue in a band pattern, which appeared to be consistent with the intercalated discs. Double staining with cadherin, a representative protein that exists in the intercalated discs, and observation using a confocal fluorescence microscope showed that LACS localization virtually matched with that of cadherin. Thus, LACS seemed to exist near the intercalated discs.

(2) Localization in Cultured Myocardial Cells

Primary cultures of myocardial cells isolated from neonatal rats (one- to three-day old) using trypsin and collagenase were prepared. For the first 24 to 48 hours, the cells were cultured in a serum-containing medium, and then for another 24 hours in a serum-free medium.

Western blot analysis of the cultured myocardial cells showed that the LACS protein was fractionated into the cytoskeletal component (TritonX insoluble fraction). In immunostaining, staining along the actin fibers, particularly near the sites of intercellular adhesion, was observed. The sites of intercellular adhesion are said to have an in vivo intercalated disc-like structure, and thus LACS was considered to exist along the actin fibers at the sites of intercellular adhesion.

These results showed that LACS is a cytoskeletal protein.

EXAMPLE 5

LACS Expression

A c-myc tag was attached to LACS, and this construct was inserted into expression vectors, pcDNA3.1 (Invitrogen) and pEGFP (CLONTECH). The obtained expression vectors were transfected into COS-1 cells using FuGene6 (Roche Diagnostics) for transient overexpression. After 48 hours, an approximately 374-kDa band, corresponding to the molecular weight predicted theoretically from the LACS nucleotide sequence, was detected by Western blotting against c-myc. Furthermore, the expression of c-myc-fused LACS protein at the cellular level was confirmed by c-myc immunostaining after immobilizing the cells.

EXAMPLE 6

LACS Expression Increases Due to Hypertrophic Agonist Stimulation on Cultured Myocardial Cells Myocardial cells cultured by the same method in Example 4 were used. First, cells were stimulated with the representative hypertrophic agonists, AngII, phenylephrine, and Endothelin-1. LAC protein expression was detected in each of the cultured cells, and was found to increase when any of the hypertrophic agonists was used.

LACS expression which increases upon phenylephrine stimulation was suppressed by the simultaneous administration of 10 μM of Y27632 (ROCK inhibitor; Calbiochem). This suggests that the Rho/ROCK system is related to the expression of LACS gene. Rho is a low-molecular-weight GTP-binding protein (small G protein) involved in the contraction of smooth muscles, and regulation of cytokinesis, cell motility, and cytomorphology, via reorganization of actin filaments.

EXAMPLE 7

Detection of Actin

Immunoprecipitation was performed using the LACS antibody to obtain precipitated proteins from cultured myocardial cells. A band corresponding to the actin protein was detected by Western blotting using an anti-actin antibody.

This result shows that LACS and actin bind to each other. Immunostaining in Example 4 suggests the possibility of LACS interacting with cadherin since its localization matches that of cadherin. However, a band corresponding to cadherin was not detected in the above-mentioned experiment, and therefore the possibility of direct binding to cadherin was rejected.

EXAMPLE 8

LACS Expression in the Carotid Arteries

Analysis of LACS mRNA expression by RT-PCR confirmed its expression in the carotid arteries. After balloon injury, mRNA expression gradually increased and peaked on the seventh day. This suggests the possibility that LACS exists in the smooth muscles. Since smooth muscles are stable and readily cultured, they are convenient for further functional analyses of LACS.

INDUSTRIAL APPLICABILITY

The present invention provides novel actin-related cytoskeletal protein LACS and genes encoding this protein. The present invention reveals that: the expression of the LACS protein is increased in the heart of several hypertension and cardiomegaly model animals; this expression increases when hypertrophic agonists are administered; and the LACS protein is bound to actin in cells. These facts suggest that the LACS protein plays a specific role in the maintenance of the cardiovascular system by enhancing or suppressing actin polymerization. Therefore, the proteins of this invention and polynucleotides encoding these proteins may be effective for the prevention, improvement, or treatment of cardiac diseases involving actin polymerization, such as cardiac failure, cardiomegaly, myocarditis, cardiomyopathy, arteriosclerosis, arteriosclerosis obliterans, and ischemic heart disease.

The invention claimed is:

1. An isolated polynucleotide encoding a protein comprising the amino acid sequence of SEQ ID NO: 1.

2. The isolated polynucleotide of claim 1, which comprises the nucleotide sequence of SEQ ID NO: 2.

3. A composition comprising the isolated polynucleotide of claim 1.

4. A composition comprising the isolated polynucleotide of claim 1 and a pharmaceutically acceptable excipient.

* * * * *